United States Patent
Mauldin et al.

(10) Patent No.: US 11,504,095 B2
(45) Date of Patent: Nov. 22, 2022

(54) THREE-DIMENSIONAL IMAGING AND MODELING OF ULTRASOUND IMAGE DATA

(71) Applicant: Rivanna Medical LLC, Charlottesville, VA (US)

(72) Inventors: Frank William Mauldin, Charlottesville, VA (US); Adam Dixon, Charlottesville, VA (US); Kevin Owen, Crozet, VA (US)

(73) Assignee: Rivanna Medical, Inc., Charlottesville, VA (US)

( * ) Notice: Subject to any disclaimer, the term of this patent is extended or adjusted under 35 U.S.C. 154(b) by 260 days.

(21) Appl. No.: 16/963,117

(22) PCT Filed: Jan. 8, 2019

(86) PCT No.: PCT/US2019/012622
§ 371 (c)(1),
(2) Date: Jul. 17, 2020

(87) PCT Pub. No.: WO2019/136412
PCT Pub. Date: Jul. 11, 2019

(65) Prior Publication Data
US 2021/0045715 A1    Feb. 18, 2021

Related U.S. Application Data

(60) Provisional application No. 62/614,559, filed on Jan. 8, 2018.

(51) Int. Cl.
*A61B 8/08* (2006.01)
*A61B 8/13* (2006.01)
(Continued)

(52) U.S. Cl.
CPC ............ *A61B 8/483* (2013.01); *A61B 8/0841* (2013.01); *A61B 8/0875* (2013.01); *A61B 8/13* (2013.01);
(Continued)

(58) Field of Classification Search
None
See application file for complete search history.

(56) References Cited

U.S. PATENT DOCUMENTS

2003/0135119 A1    7/2003  Lee et al.
2013/0116681 A1*   5/2013  Zhang ................. A61B 5/4836
                                                      606/34

(Continued)

OTHER PUBLICATIONS

Application No. PCT/US2019/012622, International Preliminary Report on Patentability dated Jul. 14, 2020 and Written Opinion dated Apr. 12, 2019.

*Primary Examiner* — Amanda Lauritzen Moher
*Assistant Examiner* — Delia M. Appiah Mensah
(74) *Attorney, Agent, or Firm* — Woods Rogers Vandeventer Black PLC; Nathan A. Evans

(57) ABSTRACT

The position and orientation of an ultrasound probe is tracked in three dimensions to provide highly-accurate three-dimensional bone surface images that can be used for anatomical assessment and/or procedure guidance. The position and orientation of a therapy applicator can be tracked in three dimensions to provide feedback to align the projected path of the therapy applicator with a desired path for the therapy applicator or to provide feedback to align the potential therapy field of a therapy applicator with a target anatomical site. The three-dimensional bone surface images can be fit to a three-dimensional model of the anatomical site to provide or display additional information to the user to improve the accuracy of the anatomical assessment and/or procedure guidance.

19 Claims, 9 Drawing Sheets

(51) Int. Cl.
  *A61B 8/00* (2006.01)
  *A61N 7/00* (2006.01)
  *G06N 3/02* (2006.01)

(52) U.S. Cl.
  CPC ............ *A61B 8/4263* (2013.01); *A61B 8/466* (2013.01); *A61B 8/5207* (2013.01); *A61N 7/00* (2013.01); *G06N 3/02* (2013.01); *A61B 2562/0257* (2013.01); *A61N 2007/0004* (2013.01)

(56) References Cited

U.S. PATENT DOCUMENTS

| | | | |
|---|---|---|---|
| 2015/0320481 A1* | 11/2015 | Cosman, Jr. ....... | A61B 18/1482 606/35 |
| 2017/0020626 A1* | 1/2017 | Schlenger ............ | A61B 8/4245 |
| 2017/0202624 A1* | 7/2017 | Atarot ................... | A61B 90/03 |
| 2017/0367766 A1 | 12/2017 | Mahfouz | |
| 2020/0281662 A1* | 9/2020 | Cong .................... | A61B 34/10 |

* cited by examiner

US 11,504,095 B2

THREE-DIMENSIONAL IMAGING AND MODELING OF ULTRASOUND IMAGE DATA

CROSS REFERENCE TO RELATED APPLICATIONS

The present application is a National Stage application under 35 U.S.C. § 371 of International Application No. PCT/US2019/012622, filed Jan. 8, 2019, which application relies on the disclosure of and claims priority to and the benefit of the filing date of U.S. Provisional Patent Application No. 62/614,559, filed Jan. 8, 2018, the disclosures of which are hereby incorporated by reference in their entireties.

STATEMENT OF FEDERALLY SPONSORED RESEARCH

This invention was made with government support under R44 EB024384 awarded by National Institute of Biomedical Imaging and Bioengineering of the National Institutes of Health. The government has certain rights in the invention.

TECHNICAL FIELD

The present application relates generally to three-dimensional rendering of bone images acquired through ultrasound imaging.

BACKGROUND

Medical ultrasound is commonly used to facilitate needle injection or probe insertion procedures such as central venous line placement or various spinal anesthesia procedures. A commonly implemented technique involves locating anatomical landmarks (e.g., blood vessel or bone structures) using ultrasound imaging and subsequently marking the patient's skin with a surgical marker in proximity to the ultrasound transducer. The ultrasound transducer is then removed, and the needle is inserted after positioning it at a location relative to the marking site.

Needle insertion, probe placement, and therapeutic delivery procedures require an understanding of the underlying three-dimensional anatomy to ensure accurate placement of the therapeutic instrument. However, existing medical ultrasound systems are most often configured to provide only two-dimensional, cross-sectional views of the underlying anatomy. As a result, it is technically challenging to execute three-dimensional navigation of the therapeutic instrument while referencing only two-dimensional, cross-sectional views of the anatomy. Further, few medical ultrasound systems provide visual cues to the medical practitioner to assist with determining whether the therapeutic device is aligned with the target anatomical site. Current systems do not provide visual guidance to the medical provider to determine whether the therapeutic device is aligned with the target therapy site, without complicated registration to other 3D imaging modality images (CT/MRI).

The limitations of existing medical ultrasound systems result in the need for medical practitioners to undergo extensive training regimens to compensate for the lack of real-time, three-dimensional image guidance information. The training burden results in a shortage of competent medical practitioners who are qualified to perform the interventional procedures.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an ultrasound imaging and therapy guidance system comprising: an ultrasound probe that generates a positionally-adjusted ultrasound beam to acquire three-dimensional image data of bone anatomy in a human subject; an object tracker configured to detect a current position and a current orientation of the ultrasound probe; a therapy applicator to deliver a therapy to the human subject; a mechanical apparatus coupled to the ultrasound probe and the therapy applicator to set a predetermined relative position of the therapy applicator with respect to the ultrasound probe; a processor; a non-transitory computer memory operatively coupled to the processor. The non-transitory memory comprises computer-readable instructions that cause the processor to: detect a position and an orientation of three-dimensional bone surface locations based at least in part on the three-dimensional image data and the current position and the current orientation of the ultrasound probe; automatically detect a target therapy site relative to the three-dimensional bone surface locations; determine an appropriate position and an appropriate orientation of the therapy applicator required to deliver the therapy to the target therapy site; and generate display data. The system also comprises a display in electrical communication with the processor, the display generating images based on the display data, the images comprising: an indication of the three-dimensional bone surface locations; an instantaneously-acquired two-dimensional ultrasound image frame that is co-aligned with a potential therapy field for the therapy applicator at a current position and a current orientation of the therapy applicator; an indication of the target therapy site relative to the three-dimensional bone surface locations; and graphical indicators that indicate whether the target therapy site and potential therapy field are aligned.

In one or more embodiments, the computer-readable instructions further cause the processor to automatically detect the target therapy site relative to the three dimensional bone surface locations using a neural network. In one or more embodiments, the computer-readable instructions further cause the processor to detect the position and the orientation of the three-dimensional bone surface locations by fitting the three-dimensional image data to a three-dimensional bone model. In one or more embodiments, the images generated by the display further include bone landmark locations. In one or more embodiments, the computer-readable instructions further cause the processor to automatically detect the target therapy site using the three-dimensional bone model.

In one or more embodiments, the indication of the three-dimensional bone surface locations are displayed as two-dimensional bone surface images with a third dimension encoded to represent a bone surface location along the third dimension. In one or more embodiments, the third dimension is graphically encoded to represent the bone surface location along the third dimension. In one or more embodiments, the third dimension is color encoded to represent the bone surface location along the third dimension.

In one or more embodiments, the appropriate position and the appropriate orientation of the therapy applicator are determined based at least in part on the predetermined relative position of the therapy applicator with respect to the ultrasound probe. In one or more embodiments, the object tracker is configured to detect the current position and the current orientation of the therapy applicator, and the appropriate position and the appropriate orientation of the therapy applicator are determined based at least in part on the current position and the current orientation of the therapy applicator.

In one or more embodiments, the images generated by the display further include a current position and a current orientation of the potential therapy field. In one or more embodiments, the images generated by the display further include the current position and the current orientation of the therapy applicator. In one or more embodiments, the images generated by the display further include dimensional and orientation information of the bone anatomy calculated from the three-dimensional bone surface locations.

In one or more embodiments, the therapy applicator comprises a needle guide, a needle, an ablation instrument, and/or a high-intensity focused ultrasound transducer. In one or more embodiments, the target therapy site includes an epidural space, an intrathecal space, or a medial branch nerve. In one or more embodiments, the ultrasound probe is configured to be positionally adjusted manually by a user. In one or more embodiments, the ultrasound probe is configured to be positionally adjusted automatically with a mechanical motorized mechanism.

In one or more embodiments, the object tracker includes inductive proximity sensors. In one or more embodiments, the object tracker includes an ultrasound image processing circuit. In one or more embodiments, the ultrasound image processing circuit is configured to determine a relative change in the current position of the ultrasound probe by comparing sequentially-acquired ultrasound images of the three-dimensional image data.

In one or more embodiments, the object tracker includes optical sensors. In one or more embodiments, the optical sensors include fixed optical transmitters and swept lasers detected by the optical sensors, the optical sensors disposed on the ultrasound probe. In one or more embodiments, the object tracker includes integrated positioning sensors. In one or more embodiments, the integrated positioning sensors include an electromechanical potentiometer, a linear variable differential transformer, an inductive proximity sensors, rotary encoder, an incremental encoder, an accelerometer, and/or a gyroscope. In one or more embodiments, the three-dimensional bone surface locations include three-dimensional spine bone locations.

In one or more embodiments, the positionally-adjusted ultrasound beam is positionally adjusted by mechanically movement of the ultrasound probe and/or electrical steering of the positionally-adjusted ultrasound beam.

Another aspect of the invention is directed to a method for guiding a therapy applicator, comprising: positionally adjusting an ultrasound beam, generated by an ultrasound probe, on a human subject to acquire three-dimensional image data of bone anatomy in the human subject; detecting, with an object tracker, a current position and a current orientation of the ultrasound probe while positionally adjusting the ultrasound beam; determining a position and an orientation of three-dimensional bone surface locations based at least in part on the three-dimensional image data and the current position and the current orientation of the ultrasound probe; automatically detecting a target therapy site relative to the three-dimensional bone surface locations; determining an appropriate position and an appropriate orientation of the therapy applicator required to deliver a therapy to the target therapy site; displaying images on a display that is in electrical communication with the computer, the images comprising: an indication of the three-dimensional bone surface locations; an instantaneously-acquired two-dimensional ultrasound image frame that is co-aligned with a potential therapy field for the therapy applicator at a current position and a current orientation of the therapy applicator; an indication of the target therapy site relative to the three-dimensional bone surface locations; and graphical indicators that indicate whether the target therapy site and potential therapy field are aligned.

In one or more embodiments, the method further comprises using a neural network in a computer to automatically detect the target therapy site relative to the three dimensional bone surface locations.

In one or more embodiments, the method further comprises fitting the three-dimensional image data to a three-dimensional bone model. In one or more embodiments, the method further comprises determining the position and the orientation of the three-dimensional bone surface using the three-dimensional bone model. In one or more embodiments, the method further comprises identifying bone landmark locations using the three-dimensional bone model. In one or more embodiments, the images comprise the bone landmark locations. In one or more embodiments, the method further comprises automatically detecting the target therapy site using the three-dimensional bone model.

In one or more embodiments, the indication of the three-dimensional bone surface locations are displayed as two-dimensional bone surface images with a third dimension encoded to represent a bone surface location along the third dimension. In one or more embodiments, the method further comprises graphically encoding the third dimension to represent the bone surface location along the third dimension. In one or more embodiments, the method further comprises color encoding the third dimension to represent the bone surface location along the third dimension.

In one or more embodiments, the method further comprises mechanically coupling a mechanical apparatus coupled to the ultrasound probe and the therapy applicator, the mechanically apparatus setting a predetermined relative position of the therapy applicator with respect to the ultrasound probe. In one or more embodiments, the method further comprises determining the appropriate position and the appropriate orientation of the therapy applicator based at least in part on the predetermined relative position of the therapy applicator with respect to the ultrasound probe. In one or more embodiments, the method further comprises detecting, with the object tracker, the current position and the current orientation of the therapy applicator; and determining the appropriate position and the appropriate orientation of the therapy applicator based at least in part on the current position and the current orientation of the therapy applicator.

In one or more embodiments, the images further include a current position and a current orientation of the potential therapy field. In one or more embodiments, the images further include the current position and the current orientation of the therapy applicator. In one or more embodiments, wherein the images further include dimensional and orientation information of the bone anatomy calculated from the three-dimensional bone surface locations.

In one or more embodiments, the therapy applicator comprises a needle guide, a needle, an ablation instrument, and/or a high-intensity focused ultrasound transducer. In one or more embodiments, the target therapy site includes an epidural space, an intrathecal space, or a medial branch nerve. In one or more embodiments, positionally adjusting the ultrasound beam comprises mechanically moving the ultrasound probe.

In one or more embodiments, the method further comprises positionally adjusting the ultrasound probe with a mechanical motorized mechanism. In one or more embodiments, positionally adjusting the ultrasound beam comprises electronically scanning the ultrasound beam.

In one or more embodiments, the object tracker includes inductive proximity sensors. In one or more embodiments, the object tracker includes an ultrasound image processing circuit. In one or more embodiments, the method further comprises, with the ultrasound image processing circuit, determining a relative change in the current position of the ultrasound probe by comparing sequentially-acquired ultrasound images of the three-dimensional image data.

In one or more embodiments, the object tracker includes optical sensors. In one or more embodiments, the optical sensors include fixed optical transmitters and swept lasers detected by the optical sensors, the optical sensors disposed on the ultrasound probe. In one or more embodiments, the object tracker includes integrated positioning sensors. In one or more embodiments, the integrated positioning sensors include an electromechanical potentiometer, a linear variable differential transformer, an inductive proximity sensors, rotary encoder, an incremental encoder, an accelerometer, and/or a gyroscope.

In one or more embodiments, the three-dimensional bone surface locations include three-dimensional spine bone locations. In one or more embodiments, the current position and the current orientation of the ultrasound probe are detected using an object tracker.

In one or more embodiments, the method further comprises acquiring two-dimensional ultrasound image data of the bone anatomy at a plurality of ultrasound probe locations; and combining the two-dimensional ultrasound image data and the ultrasound probe locations to form the three-dimensional image data. In one or more embodiments, the two-dimensional image data includes pixels and the method further comprises determining a three-dimensional position of each pixel based on the ultrasound probe locations. In one or more embodiments, the method further comprises performing bone enhancement processing to enhance any bones and/or bony features in the ultrasound images.

In one or more embodiments, the method further comprises receiving a user-interface event; and recording a fiducial position of the ultrasound probe based on a time that the user-interface event is received.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

Figure 1:
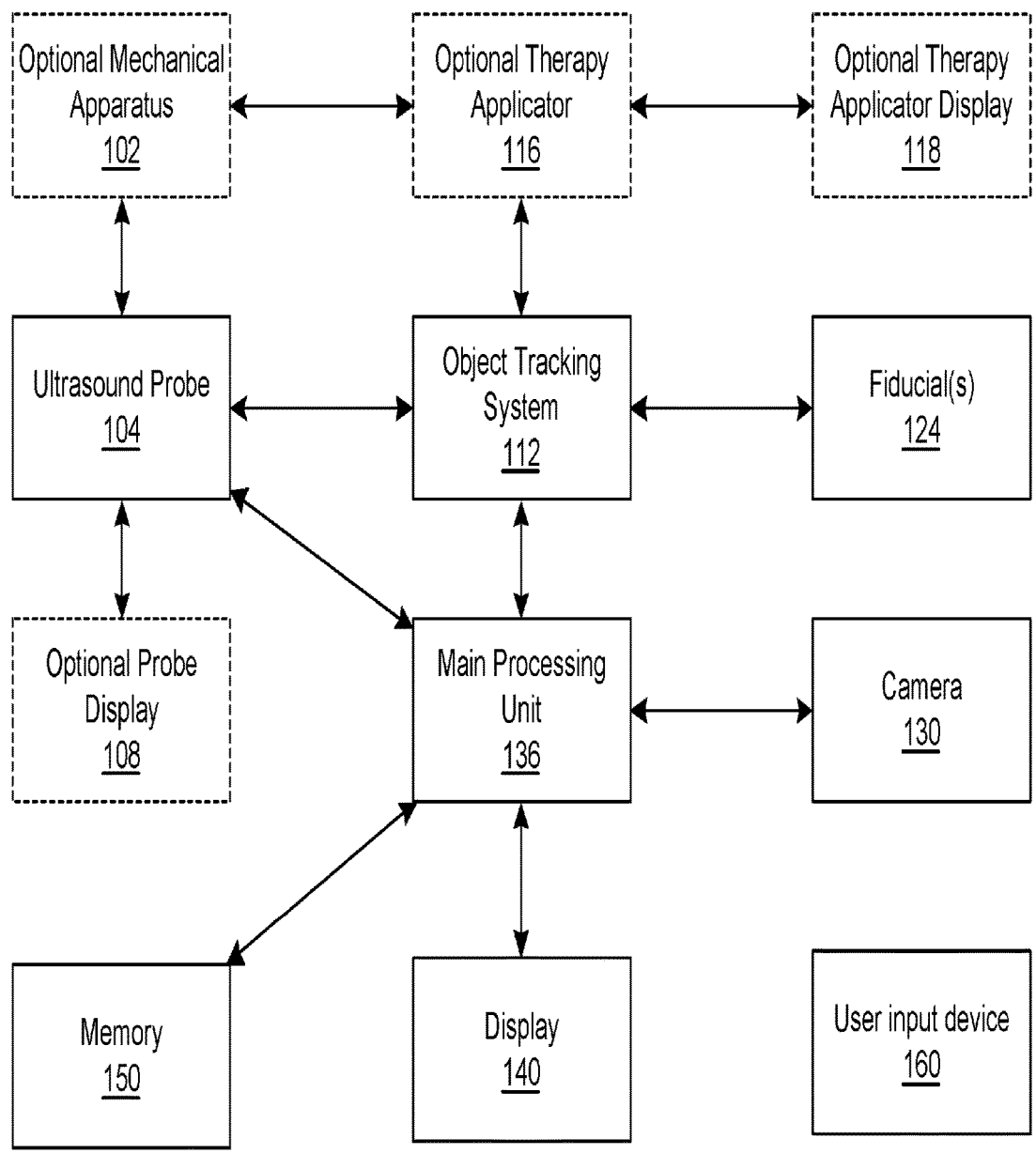
FIG. 1 is a block diagram of a system for guiding an ultrasound probe and a therapy applicator according to one or more embodiments.

Aspects of the invention are directed to an ultrasound system combined with three-dimensional (3D) position tracking that enables highly accurate 3D bone surface rendering for the purpose of anatomical assessment and/or procedure guidance (e.g., to guide a therapy applicator such as a needle and/or device during energy-based ablation). In some embodiments, the invention includes one or more of features (a)-(e). Other embodiments can include additional, fewer, and/or different features.

In feature (a), a 3D bone image can be generated by tracking (e.g., with a position tracking system) the spatial location, and optionally the orientation, of an ultrasonic probe as it is positionally adjusted proximal to a target area on a human subject (e.g., to acquire image data of bone anatomy proximal to the target area). The 3D bone image can be automatically annotated such as by providing indications of joint or bony feature locations, bone fracture locations, indications of optimal needle insertion angles, indication of possible needle or therapy sites, and/or indications and degree of scoliosis and/or other bony anatomy abnormalities.

In feature (b), the 3D bone image is fit to a model of the target anatomy and the model may be optionally displayed along with the actual bone locations.

In feature (c), real-time feedback can be provided to the user during ultrasound probe scanning (e.g., while the 3D bone image is acquired) so that 3D anatomy proximal to the target area is scanned in all locations and/or orientations required to provide a 3D display of the reconstructed bone with annotations and/or model fitting information.

In feature (d), the position tracking system tracks the therapy applicator in addition to the ultrasound transducer. After the 3D bone information is constructed, the system can provide real-time guidance of the therapy applicator to a desired location. For example, the therapy applicator can be a needle, a needle guide, a catheter, an ultrasound system or probe (with or without a needle guide), a radiofrequency ablation probe, or a high intensity focused ultrasound (HIFU) transducer. A desired therapy site could be the epidural space, facet joint, or sacroiliac joint. In some embodiments, the real-time guidance can include guiding the therapy applicator while the therapy is being applied, such as during an energy-based ablation. The desired location can be a location specified by the user, such as by indicating a location on the 3D bone reconstruction where therapy should be applied. The system would then guide the therapy applicator to the location required in order for the desired therapy site to receive the therapy when the therapy applicator is activated. Alternatively, the location can be automatically provided by the system. The location can be an optimal location for the therapy applicator to accurately deliver the therapy to the desired therapy site, or could provide several choices for an optimal location (for example, at different intervertebral spaces).

In feature (e), the ultrasound system, 3D bone locations, and/or therapy applicator can be shown in a virtual-reality (VR) environment, an augmented-reality (AR) environment, or a mixed reality (MR) environment. Any of these environments can be displayed on a VR headset, and/or a conventional computer screen, and/or on a screen attached to the ultrasound probe, and/or on a screen attached to the therapy applicator.

In VR, a simulated 3D environment can be presented to the user where stereoscopic head-mounted displays and/or some other visual stimulus method is/are used to create the illusion of depth. If the display is incapable of conveying depth information, then the VR display is simply a virtual 3D environment presented on a two-dimensional (2D) display (e.g. a monitor). This display limitation also applies to the following definitions for AR and MR systems.

In AR, some version of reality can be presented to the user with simulated ('virtual') 2D or 3D data overlaid into the visual environment. The combination of the real and virtual content can be achieved using cameras to capture the real content, and/or by combining the virtual content with the user's regular vision using transparent screens and/or other methods to inject visual information into the user's field of view. The visual environment can include a simulated 3D environment or a virtual 3D environment as described above with respect to VR.

MR is similar to AR, with real and simulated content presented seamlessly to the user, however in this modality the virtual and augmented entities can interact in real-time. For example a virtual ball can bounce off a real physical wall, or augmented anatomical information can move in space as a physical object position is sensed (e.g. skin surface). For the purpose of this application, AR includes MR as a subset thereof.

FIG. 1 is a block diagram of a system 10 for guiding an ultrasound probe and a therapy applicator according to one or more embodiments. The system 10 includes an optional mechanical apparatus 102, ultrasound probe 104, an optional probe display 108, an object tracking system 112, an optional therapy applicator 116, an optional therapy applicator display 118, a fiducial 124, a camera 130, a main processing unit 136, a display 140, a computer memory 150, and a user interface device 160.

The ultrasound probe 104 includes one or more ultrasound transducers to image a target anatomical region in a subject. An example ultrasound transducer may be a single element transducer, linear array, curvilinear array, two-dimensional array, capacitive micromachined ultrasonic transducer (CMUT), all of which are commercially available and known to those skilled in the art. In operation, a user places the ultrasound probe 104 on the subject's skin proximal to the target anatomical region, for example in advance of a treatment procedure (e.g., an epidural anesthesia procedure, an ultrasound therapy procedure, a surgical procedure, etc.) or as part of a diagnostic procedure (e.g., a spinal anatomy analysis). The user then moves or scans (e.g., mechanically and/or electronically), through positional adjustments, the ultrasound probe 104 along the subject's skin, in the vicinity of the target anatomical region, to acquire ultrasound images of the target anatomical region. By positionally adjusting the ultrasound probe 104, the ultrasound beam used to produce the ultrasound image is also positionally adjusted. In another exemplary embodiment, where a two-dimensional array transducer is utilized, then the ultrasound beam produced by the ultrasound transducer can be positionally adjusted electronically using a programmable electronic transmit circuit, which applies time delays to particular elements of the two-dimensional array (e.g., adjusting the relative phase of the driving signals to particular elements of the two-dimensional array). Such operations of two-dimensional transducer arrays to produce three-dimensional ultrasound image data without requiring mechanical movements is known to those skilled in the art and readily available commercially. In this same embodiment, the positional adjustment of the ultrasound beam is tracked from knowledge of the time delays applied to the elements within the two-dimensional array, for example as disclosed in U.S. Pat. No. 6,419,633, titled "2D Ultrasonic Transducer Array for Two Dimensional and Three Dimensional Imaging," and U.S. Pat. No. 5,329,496, titled "Two-dimensional Array Ultrasonic Transducers," which are hereby incorporated by reference. The acquired ultrasound images can be displayed on optional probe display 108 (which is disposed on or integrated into the ultrasound probe 104) and/or on display 140.

During ultrasound imaging, the ultrasound probe 104 is tracked in three-dimensional space with the object tracking system 112. The object tracking system 112 can typically track the ultrasound probe 104 in three-dimensional space using a variety of methods. For example, 3D tracking can be enabled by tracking two or more locations on the ultrasound probe 104, which in some embodiments can include tracking two or more locations on a rigid part of the ultrasound probe 104. The object tracking system 112 may also track the ultrasound probe 104 along only one or two dimensions if the ultrasound probe 104 is mechanical constrained in other dimensions such as through a mechanical frame or guide such as implemented in commercially available three-dimensional wobbler ultrasound transducers. In addition, or in the alternative, the object tracking system 112 can track the ultrasound probe 104 in three-dimensional space by tracking its position and orientation using integrated positioning sensors (e.g., that project gravitational force onto 3 perpendicular axes). Additionally, the object tracking system 112 can optionally utilize an ultrasound-data processing circuit to compute relative changes in position by comparing sequentially acquired 2D images and/or 3D volumes using speckle tracking and/or image similarity tracking techniques, commonly-known techniques in the art. For example, these techniques are described in U.S. Pat. No. 6,012,458, titled "Method and Apparatus for Tracking Scan Plane Motion in Free-hand Three-dimensional Ultrasound Scanning Using Adaptive Speckle Correlation," and U.S. Pat. No. 6,728,394, titled "Dynamic Measurement of Object Parameters," which are hereby incorporated by reference.

The object tracking system 112 can determine the position and orientation of the ultrasound probe 104 using an optical tracking system, a magnetic-based tracking system, a radio or acoustic tracking system, a camera-based tracking system, position sensors, and/or an ultrasound image processing circuit. The optical tracking system can include one or more fixed optical transmitters with optical sync pulses followed by swept lasers detected by optical sensors on the target device (i.e., the ultrasound probe 104). An example of such an optical tracking system is the HTC Vive™ Lighthouse tracking system, available from HTC Corporation of Taiwan.

The magnetic-based tracking system can include multiple pairs of fixed and mobile coils or other magnetic field sensors that can be used to determine the relative positions of the mobile coils based on variable mutual inductance of each pair of fixed and mobile coils or magnetic field measured by sensors. The mutual inductance or magnetic field value is a function of the separation distance between each pair of fixed and mobile coils, or sensors. Examples of magnetic field 3D tracking systems include those described in U.S. Pat. No. 6,774,624, titled "Magnetic Tracking System," which is hereby incorporated by reference, and those in tracking products sold by Polhemus (Colchester, Vt., USA) and NDI Medical, LLC (Ontario, Canada).

The radio or acoustic tracking system can track the position of objects on a smaller scale using the time-of-flight between fixed transmitters and mobile receivers (and/or fixed receivers and mobile transmitters), including optionally using correlation methods for fine-tuning distance estimates. The transmitters can transmit radio frequency signals or acoustic energy, and in general use time-of-flight delays and/or variations in received waves and a propagation model to estimate position and/or orientation, with sensing range and accuracy only fundamentally limited by signal to noise ratio. In some embodiments, the radio or acoustic tracing system can function similar to a global positioning system (GPS).

The camera-based tracking system includes one or more cameras attached to either or both the fixed and mobile objects. Images from the camera(s) can be analyzed to determine the relative positions of fixed and mobile structures or objects within the field of view of the camera(s).

In some embodiments, position sensors can be integrated or disposed on or in the ultrasound probe 104 (e.g., in the housing of ultrasound probe 104) or the ultrasound probe 104 can be attached or affixed to an object that includes such position sensors (e.g., integrated therein or disposed on or in the object) and the distance between the object and the ultrasound probe 104 is known. The position sensors are capable of tracking the ultrasound probe's relative motion through 3D space. Examples of position sensors include electromechanical potentiometers, linear variable differential transformers, inductive proximity sensors, rotary encoders, incremental encoders, and inertial tracking using integrated accelerometers and/or gyroscopes.

In addition or in the alternative, the 2D and/or 3D position of the ultrasound probe 104 can be tracked using speckle tracking or other image-processed based approaches for motion tracking on sequentially acquired 2D/3D ultrasound datasets (e.g. block tracking). Such ultrasound image-based tracking can be performed, at least in part, by an ultrasound image processing circuit disposed in or operatively connected to the object tracking system 112.

In some embodiments, an optional mechanical apparatus 102 can be used to constrain the position of the therapy applicator 116. This mechanical apparatus 102 would set the position of the ultrasound probe 104 relative to the therapy applicator 116. If the exact dimensions of the mechanical apparatus are known, then the exact position of the therapy applicator relative to the ultrasound probe is also known. An example of such mechanical apparatus is that which is integrated into commonly utilized ultrasound needle guides. Such needle guides have a clamp or similar mechanical mechanism, which fixes the position of the needle guide relative to the ultrasound probe. Other examples may be a mechanical frame that holds both ultrasound probe 104 and a high intensity focused ultrasound (HIFU) therapy applicator 116.

Figure 6:
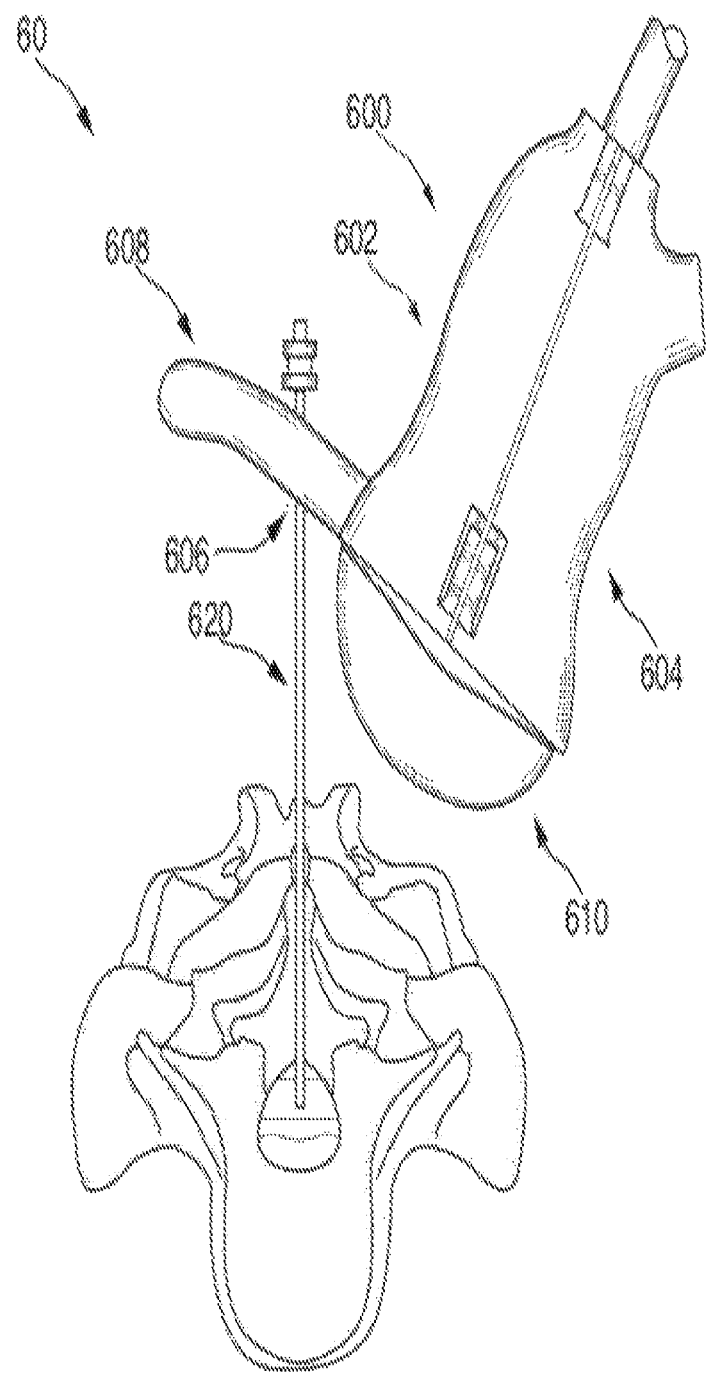
FIG. 6 is a perspective view of a mechanical system that includes a mechanical apparatus that is mechanically coupled to an ultrasound probe and a needle.

FIG. 6 is a perspective view of a mechanical system 60 that includes a mechanical apparatus 600 that is mechanically coupled to an ultrasound probe 610 and a needle 620. The mechanical apparatus includes first and second sections 602, 604 that are removably attached (e.g., with a clamp, screw, or other attachment mechanism). The first and second sections 602, 604 are disposed around the ultrasound probe 610 to rigidly retain the ultrasound probe 610 therebetween. The needle 620 passes through a hole 606 that is defined in an arm 608 of the first portion 602 of the mechanical apparatus 600. The mechanical apparatus 600 therefore sets the relative positions and orientations of the ultrasound probe 610 and a needle 620. It is noted that needle 620 can be another therapy applicator (e.g., therapy applicator 116) in other embodiments.

Returning to FIG. 1, The data output of the ultrasound probe 104 and the object tracking system 112 are provided to a computer that includes a main processing unit 136. The main processing unit 136 can process this data and output image data to display 140 and/or to optional probe display 108, as described herein. Display 140 can be a two-dimensional display (e.g., a computer monitor) or a three-dimensional display, such as a virtual reality headset that can be worn by the user.

The object tracking system 112 can also track the optional therapy applicator 116 and/or fiducial marker(s) 124 in three-dimensional space. The object tracking system 112 can track the therapy applicator 116 in three-dimensional space in the same or substantially the same way as it tracks the ultrasound probe 104. The fiducial marker(s) 124 can be markers in absolute space independent of subsequent subject movement and/or they can be markers that are physically attached to an object (e.g., the ultrasound probe 104 and/or the therapy applicator 116) and therefore can be subsequently tracked as the fiducial markers move. In some embodiments, the fiducial marker(s) can be physically attached to the human subject. The object tracking system 112 can track the three-dimensional position and optional orientation of the fiducial marker(s) 124 in three-dimensional space as further described below.

A camera 130 is in electrical communication with the main processing unit 136. The camera 130 can be static (i.e., a camera mounted at a fixed position) or dynamic, such that its location is also tracked in 3D space (e.g., a camera worn by the user, such as a front-facing camera that is part of a virtual reality headset, such as the HTC Vive™ headset). The camera 130 can be used to capture images of the human subject and/or device user so that, for example, if a virtual reality headset is used in a procedure on the subject's back, the human subject's back can be displayed along with the device user's arm holding the therapy applicator 116 in addition to other information (e.g., 3D spine model fit, 3D bone composite image, fiducial(s) 124, user annotations, analytics, and/or the therapy applicator 116, amongst other items).

Alternatively, the therapy applicator 116 may contain integrated position sensors or may be affixed to a mechanism containing integrated position sensors that are capable of tracking the position of the therapy applicator 116 position through 3D space and the relative position of the therapy applicator 116 with respect to the ultrasound probe 104. As an example, the therapy applicator 116 may be a needle, which may be affixed to a needle guide that is rigidly mounted to the ultrasound probe 104. The needle guide may contain a rotary encoder mechanism by which the relative angular trajectory of the needle with respect to the ultrasound probe may be measured. Additionally, the needle's linear advancement through the needle guide and into the human subject may be measured by a linear variable differential transformer that is integrated into the needle guide.

The computer memory 150 includes non-transitory computer memory that is operatively coupled to the main processing unit 136. The memory 150 can store computer programs or applications, instructions, and/or datasets that can allow the main processing unit 136 to perform the functionality described herein.

The user interface device 160 can include a mouse, a touchscreen, a virtual button, a mechanical button, a microphone (e.g., to receive voice commands), or other device that allows a user to interact with the computer.

Figure 2:
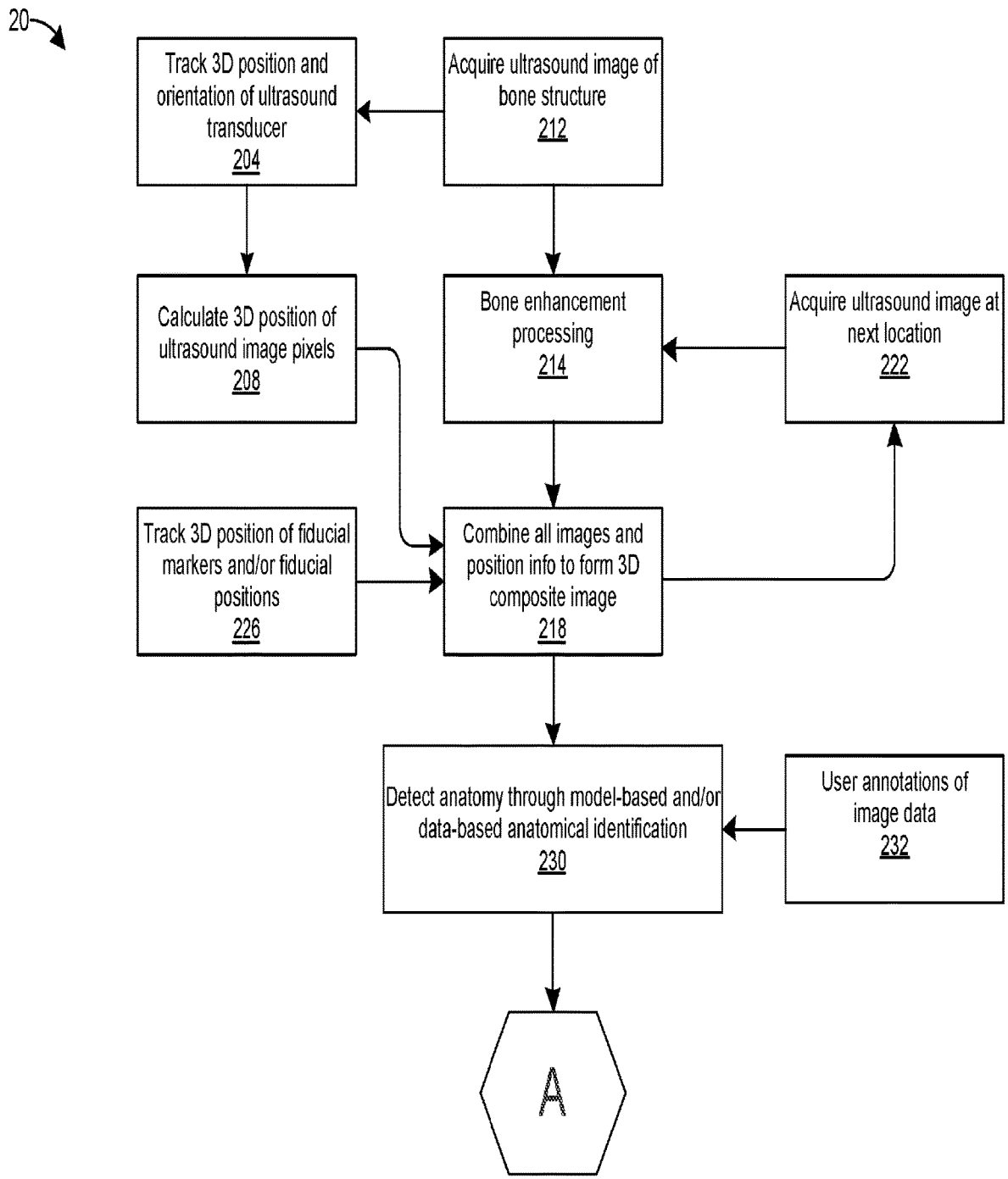
FIG. 2 is a flow chart that illustrates a method for tracking and/or guiding an ultrasound probe and a therapy applicator according to one or more embodiments.
Figure 2:
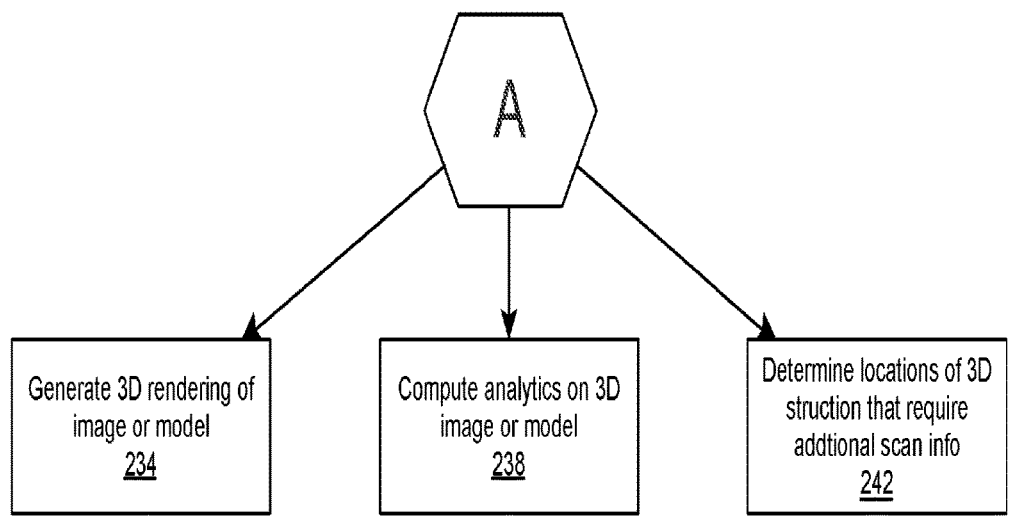
Figure 2:
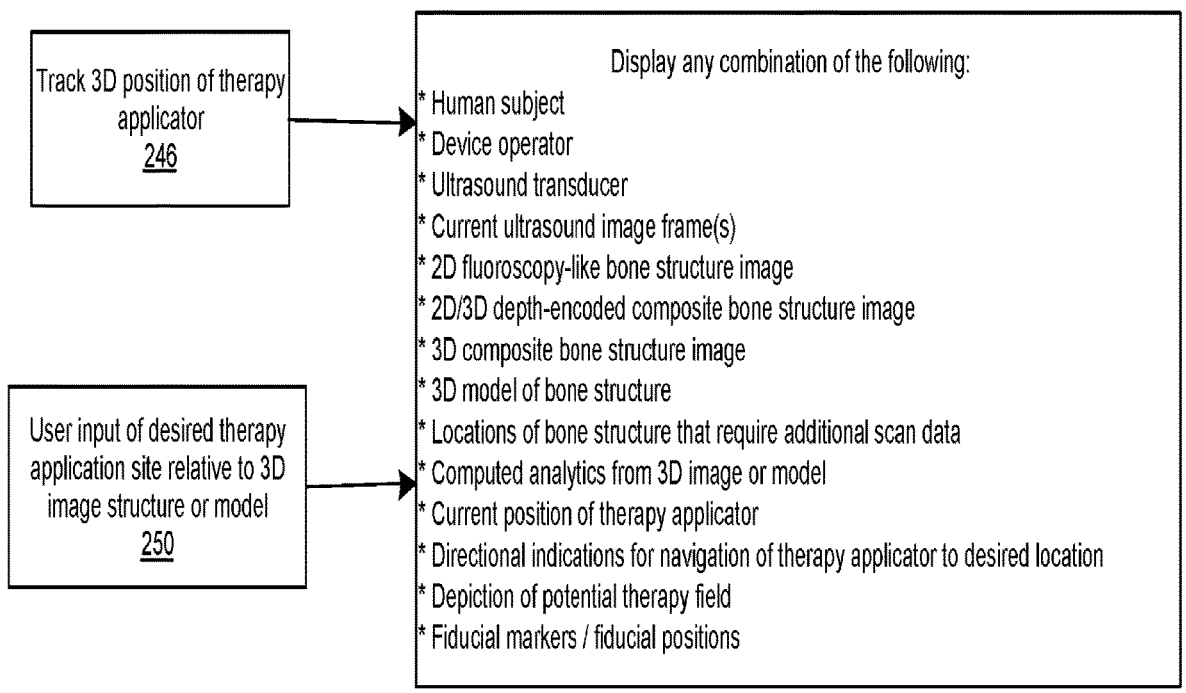

Other aspects of system 10 will be described in connection with flow chart 20 in FIG. 2 which illustrates a method for tracking and/or guiding an ultrasound probe and a therapy applicator according to one or more embodiments.

In step 204, the three-dimensional position and orientation of ultrasound probe 104 is tracked as the ultrasound probe 104 user places it on and/or moves it along the human subject's skin proximal to a target anatomical region. The three-dimensional position and orientation of ultrasound probe 104 can be tracked using the object tracking system 112 as discussed above.

In step 208, the main processing unit 136 calculates the three-dimensional position of the ultrasound image pixels. The locations of ultrasound image pixels in a one-dimensional (1 D), two-dimensional (2D), or three-dimensional (3D) space have a spatial relationship relative to the position and orientation of the ultrasound probe 104 (e.g., ultrasound transducer) at a particular instant in time. For example, at an instant in time, the position and orientation of the ultrasound probe can be described by a 3-dimensional position vector (e.g. $r_0=[0.5\ m,\ 1.0\ m,\ 1.0\ m]$ in x, y, z axes) and a set of three orthogonal unit vectors (e.g., i, j, k) such that each individual ultrasound pixel 'n' (out of N total) has a position in space described by $r_n=r_0+a_n i+b_n j+c_n k$, where $a_n$, $b_n$ and $c_n$ describe the pixel position relative to the probe in three arbitrary but fixed orthogonal axes. Using this information, a linear transform in 3D space can be constructed to calculate the instantaneous position of each of the ultrasound image pixels for a 1 D, 2D, or 3D ultrasound image.

The imaging field of view and the ultrasound image pixels (e.g., 'n') can occupy a known region of space that is projected from the ultrasound transducer elements. The spatial relationship between the probe and the field of view can be derived from a known geometrical relationship, inherent to the ultrasound probe design. In some embodiments, the ultrasound probe can create a 3D image natively. In other embodiments, the ultrasound probe forms a 3D image by combining individual 2D images.

In step 212, the ultrasound probe 104 acquires ultrasound images of the target anatomical region at a first location, which can include bones and/or bony features. After the ultrasound images are acquired, the main processing unit 136 performs bone enhancement processing in step 214 to enhance any bones and/or bony features in the ultrasound images. Bone enhancement processing can be performed using any method known in the art, such as phase coherence between adjacent ultrasound echoes from the same bony surface, directional log-Gabor filtering, and rank-reduction methods that also enhance bone reflections. In another example, bone shading, bone shadowing, and other physical aspects of the acoustic/ultrasound interaction with bony structure can be used to enhance the bony features, for example as described in U.S. Patent Application Publication No. 2016/0012582, titled "Systems and Methods for Ultrasound Imaging," published on Jan. 14, 2016, U.S. Patent Application Publication No. 2016/0249879, titled "Systems and Methods for Ultrasound Imaging of Regions Containing Bone Structure," published on Sep. 1, 2016, and/or PCT Application No. PCT/US17/47472, titled "System and Method for Ultrasound Spine Shadow Feature Detection and Imaging Thereof," filed on Aug. 18, 2017, which are hereby incorporated by reference.

In optional step 226, fiducial marker(s) 124 is/are generated and tracked. Using the tracked ultrasound probe 104 of step 204 in optional contact with the patient, a user-interface event can be used to record the instantaneous position and orientation of the ultrasound probe 104 so that some extremity of the ultrasound probe 104 corresponds to a fiducial position (e.g., as a fiducial marker 124). For example, the tip of the ultrasound probe 104 can be positioned at the sacrum or alternatively at the bony protrusion above the intra-gluteal cleft, and then a user-interface button can be pressed to record a fiducial position (e.g., as a fiducial marker 124) of the tip of the ultrasound probe 104. Additionally, by capturing several or many fiducial markers 124 associated with a single object, a surface may be captured, for example the skin surface of the back or the length of the ultrasound probe 104.

In one example, the three-dimensional position(s) of the fiducial marker(s) 124 and/or fiducial position(s) are tracked using the object tracking system 112 and/or a static camera (e.g., camera 130). The three-dimensional position(s) of the fiducial marker(s) 124 and/or fiducial position(s) can be tracked using a similar method to the ultrasound probe 104 tracking of step 204. As discussed above, a user-interface button can be activated to indicate the location of a fiducial maker 124 in space which can be tracked with the objecting tracking system 112 and/or static camera (e.g., camera 130).

In another example, the three-dimensional position(s) of the fiducial marker(s) 124 and/or fiducial position(s) can be tracked using a similar method to the ultrasound probe 104 tracking of step 204. A trackable object can be attached to the human subject's skin and the trackable object can be used as a permanent fiducial marker 124 that will track the subject's motion in real time.

In yet another example, the three-dimensional position(s) of trackable or fixed-position objects, which can operate as fiducial markers 124, attached to the subject's skin can be tracked with a camera (e.g., camera 130) and/or the object tracking system 112. In some embodiments, the objects attached to the subject's skin can include stickers with spatially-encoded identification and/or color-coded identification. The spatially-encoded identification and/or color-coded identification can be used to determine the instantaneous position of the tracked object (e.g., sticker) and knowledge of the geometry of the camera imaging can be used to track the fiducial position(s) in real-time as the subject and object(s) move. The camera can be a spatially-fixed camera or a "dynamic" camera, such as a front-facing camera on a virtual reality headset.

In step 218, the images and position information are combined to form a 3D composite image. In this step, the outputs of steps 214 and 208—respectively the bone-enhanced ultrasound data sets from successive capture and the 3D positions of each pixel from each capture—are combined to produce a set of bone-enhanced ultrasound pixels, each pixel corresponding or registered to a specific location in 3D space. This processing can be performed by and/or can be related to the ultrasound probe 104, the 3D object tracking system 112, the main processing unit 136, and optionally the fiducial marker(s) 124. The position information includes bone-enhanced ultrasound data in addition to optional fiducial positions. Step 218 is generally referred to as "freehand" 3D imaging by those skilled in the art of ultrasound.

In some embodiments, step 218 can include using the 3D position information, provided by the object tracking system 112, of the ultrasound probe 104 to perform a gross registration of the 2D frames of ultrasound image data into a 3D volume. This can be accurate to approximately 1 mm in some embodiments.

In addition or in the alternative, step 218 can include a data-dependent frame-to-frame registration operation (e.g., speckle tracking) to better align the image features in 2D frames of ultrasound image data into a 3D volume. This would be an iterative, semi-rigid registration operation that would preserve spatial relationships between image features, but reduce the registration error to approximately sub-millimeter errors.

In addition or in the alternative, step 218 can include applying some sort of persistence mapping or other method to improve specificity of bone feature detection in regions of the volume that are sampled multiple times. The persistence mapping or other method can exclude false-positive bone features that are not present in all samples of the same region.

Techniques for combining images and position information to generate a 3D composite image have been described, for example, in the following documents, which are hereby incorporated by reference: (1) R. Rohling, A. Gee, L. Berman, "A comparison of freehand three-dimensional ultrasound reconstruction techniques," Medical Image Analysis, 3(4): 339-359, 1999; and (2) O. V. Solberg, F. Lindseth, H. Torp, R. E. Blake, T. A. N. Hernes, "Freehand 3D ultrasound reconstruction algorithms—a review," Ultrasound in Medicine & Biology, 33(7): 991-1009, 2007.

There are several additional ways to produce the 3D composite image in step 218, as illustrated by the following examples, which may be used singly or in some arbitrary combination. For example, the data sets from each bone-enhanced ultrasound capture (e.g., output of step 214) can be treated as standalone subsets of 3D samples, which can be searched and analyzed in future processing steps. In another example, if the data sets from each bone-enhanced ultrasound capture are treated as scalar values placed in a 3D space, then the spatial frequency characteristics of the data set can be employed along with Nyquist-Shannon sampling theory to resample the 3D data so that a uniform or non-uniform 3D scalar field is produced in order to simplify further analysis.

In yet another example, the data sets from each bone-enhanced ultrasound capture can be treated as vector values, as each scalar value from an individual ultrasound frame also has an associated direction of the corresponding acoustic wave front, given by acoustic propagation theory. The bone-enhanced pixel values from step 214 can have varying sensitivity based on the angle the acoustic wave vector makes with the bone surface. This means that a vector data set in the 3D space contains richer information that can be used to improve subsequent analysis.

The data sets from each bone-enhanced ultrasound capture (e.g., output of step 214) can be combined with the 3D data set resulting from the previous 2D scans using several methods, which may be used singly or in some arbitrary combination, such as in examples (a)-(c) below.

Example (a) includes additive combination of the 3D data, for example supporting a "density" function in 3D space.

Example (b) includes using the existing 3D data as a "prior" probability of the three-dimensional bone surface location in space. The data from an individual scan can be used to iteratively update the 3D bone-surface probability function in space. Furthermore, in order to filter out "false-positive" bone surfaces (e.g., caused by loss of ultrasound probe contact), the 3D bone-surface probability volume function may also have an "age" parameter. The age parameter can be used to retire bone surface locations with fairly low probability (e.g., less than 25%) do not get reinforced by subsequent scans (increasing their probability) within a certain amount of time (e.g., within a certain number of scans). This probability data can also improve the accuracy of real bone surfaces, that are made up of several to many scans, with the location in space and bone detection effectively being averaged or compounded over lots of partially-independent measurements. The treatment of compounded bone probabilities may be a nonlinear function of existing and new-scan probability, and the age history of scans that formed the existing probability.

Example (c) includes using other prior bone probabilities. For example if a skin surface fiducial marker and/or some bony fiducial markers (e.g. hip anatomy) are identified, these can be used to modify bone likelihood in space. Similarly, once the 3D model of optional step 230 has been at least partially-constructed, this may also modify bone probabilities, for example making bone surfaces more likely near anatomy identified as spinous process by the model, and less likely near anatomy identified as intervertebral space by the model.

In step 222, ultrasound image data is acquired at a next or subsequent location (i.e., after the ultrasound image is acquired at a first location in step 212). The ultrasound probe 104 is capable of capturing ultrasound data sets at successive positions and at successive times, with some control and/or reporting of the time that the data sets are captured, so they can be registered in space (e.g., in steps 208 and 218). This can be accomplished, for example, by controlling the timing of data captures to coincide with physical positions, or by continuous repetitive capture of ultrasound frames along with accurate recording of their timing relative to the motion tracking sample instants. The ultrasound probe 104, the object tracking system 112, and the main processing unit 236 can be involved in this processing step.

In step 230, landmark anatomy is detected automatically through a model-based or data-based algorithm. In one embodiment, this may include a model-fitting algorithm that matches the composite 3D image (e.g., output of step 218) to a 3D model, for example as disclosed in U.S. Pat. No. 10,134,125, titled "Systems and Methods for Ultrasound Imaging," which is hereby incorporated by reference. In some embodiments, the 3D composite image formed in step 218 is fitted to a 3D model with optimization to meet certain constraints. Such constraints can include prior knowledge of the type of anatomy imaged, for example lumbar spine, thoracic spine, or other specific bony anatomy.

A shape model-based approach may therefore be used. Shape models typically identify points of interest in the image (e.g., bone points or surfaces) and compare these to one or more prototypical set(s) of points or surfaces (e.g., templates) that conform to a shape of, for example, known anatomical features. Linear and/or non-linear transforms may be parametrically applied to the shapes or templates and used to match against the points of interest in the image, with closeness of fit used as a metric to determine whether the image matches a particular anatomy. Further constraints can include parts of the anatomy tagged as fiducial markers 124 (and tracked in step 226), e.g., a particular vertebra(e), pelvic extremities, etc. In addition, prior statistical knowledge of the target anatomy and mechanical constraints can be used to aid 3D model fitting, for example statistical distribution of vertebral dimensions, separation distances between bones (e.g., between adjacent vertebrae), and/or inter-vertebral bending angles.

Model-fitting and registration techniques are known to those skilled in the art of ultrasound and/or image processing. For example, open source software such as Insight Segmentation and Registration Toolkit (https://itk.org/), available from the U.S. National Library of Medicine, provides access to 3D registration software using algorithms such as point set registration among other methods. Furthermore, pre-existing images of any modality can be used to constrain the 3D model fitting, such as applying a CT and/or MRI data set to restrict the 3D model parameters.

There are a number of methods that could be used in the optimization process of 3D model fitting, such as in Optimization Examples (1)-(3).

Optimization Example (1) includes a parameter space search. For example, a heuristic, linear, and/or adaptive search of parameter space for the 3D model, such as by changing parameters such as vertebral position, size, and/or orientation until there is a good fit in a least-squares sense to the observed data from step 218.

Optimization Example (2) includes maximum likelihood model fitting using prior knowledge and Bayesian analysis. This example can be implemented by exploring the parameter space of a constrained 3D model (such as a multi-vertebral spine) and finding the set of parameters (e.g., location, orientation, and/or size parameters of each vertebra) that maximizes the probability that the input data set (from step 218) would arise from a given 3D model parameter set given the a priori likelihoods of any given parameter set.

Optimization Example (3) includes deep learning approaches of varying design (e.g., neural networks, convolutional neural networks, and/or Bayesian inference convolutional neural networks). Such deep learning approaches can be used after sufficient training to implement deep learning analysis to both classify the observed data as belonging to a particular anatomy (e.g., lumbar vertebrae, sacrum) and to identify individual 2D and/or 3D features within the observed data that correspond to a "good fit" of the observed data based on the training set.

In step 230, the 3D bone model fit and the 3D image of bone anatomy may be optionally used as a prior probability model for a secondary model fit to nearby soft-tissue anatomical structures. In some embodiments, the soft-tissue structure may be the target of a therapeutic intervention (e.g., shoulder bursa) and in others it may simply provide additional anatomic information to assist with the medical procedure (e.g., location of lungs). Soft tissue information contained in the 2D ultrasound image acquired in step 212 may be post-processed to extract image features (e.g., edge detection, shape detection) prior to being fitted to a 2D or 3D model with optimization to meet certain constraints. Such constraints can include the anatomical information contained in the 3D bone model fit and the 3D image of bone anatomy. Additionally, constraints may include prior knowledge of the type of anatomy imaged, for example shoulder joint, thoracic spine, rib cage, or other specific bony anatomy. Further constraints can include parts of the anatomy tagged by fiducial marker(s) 124 (and tracked in step 226), e.g. a particular vertebra, pelvic extremities, joint locations, etc. In addition, prior statistical knowledge of the target anatomy and mechanical constraints can be used to aid 3D model fitting, for example statistical distribution of rib or vertebral dimensions, separation distances between bones (e.g., between adjacent vertebrae), and/or inter-vertebral bending angles. Furthermore, pre-existing images of any modality can be used to constrain the 3D model fitting, such as applying a CT and/or MRI data set to restrict the 3D model parameters. There are a number of methods that could be used in the optimization process of 3D model fitting, such as in the examples listed above.

In step 232, a user can annotate the image data. The image data is preferably displayed in human-readable form, with the ability to manipulate the view (zoom, pan, rotate, change projection, etc.) so that the user can annotate 3D positions, lines, areas, and/or volumes in the 3D model. Any annotations performed by the user are co-registered with the 3D image data and/or the 3D model so that in subsequent processing steps the annotations can be used seamlessly with the other data sources.

In step 234 (via placeholder A in flow chart 20), a 3D rendering of the images and/or model is generated for display on a display (e.g., display 140 and/or optional probe display 108). In this step, some combination of the 3D composite image formed in step 218, the 3D model from step 230, and/or user annotations from step 232 are rendered under user controls (zoom, pan, rotate, etc.) so that a user can usefully view the entire 3D registered data set or some subset thereof. The different components in the display (e.g., display 140 and/or optional probe display 108) can be rendered in various different ways consistent with the state of the art in 3D rendering, for example as in the following methods.

In general, the simplest way to achieve 3D rendering is using a 3D rendering framework such as OpenGL® (available from The Kronos Group Inc.), Unity® (available from Unity Technologies ApS), Unreal® (available from Epic Games, Inc.) or similar, optimized to render surfaces, points, and objects in 3D space with custom textures, lighting, etc. Various 3D rendering algorithms and toolkits are readily available and known to those skilled in the art of ultrasound and/or image processing. These include The Visualization Toolkit® (https://www.vtk.org/).

As described above, the 3D rendering may take the form of a fully-interactive 3D volume in which the user may zoom, pan, or rotate the entire volume. The 3D volume may also be configured to be viewed from a specific vantage point, for example, in the case of viewing spine anatomy, along the posteroanterior line-of-sight to provide a "birds-eye" view of the vertebral column. In this case, the 3D volume may be rendered as a maximum intensity projection within this plane, or as a two-dimensional image with the third dimension encoded to indicate each bone surface's value in the third dimension. For example, the third dimension can be graphically encoded such as by a color mapping, contours, or other graphic that is attributed to each bone surface's value in the third dimension.

Figure 7:
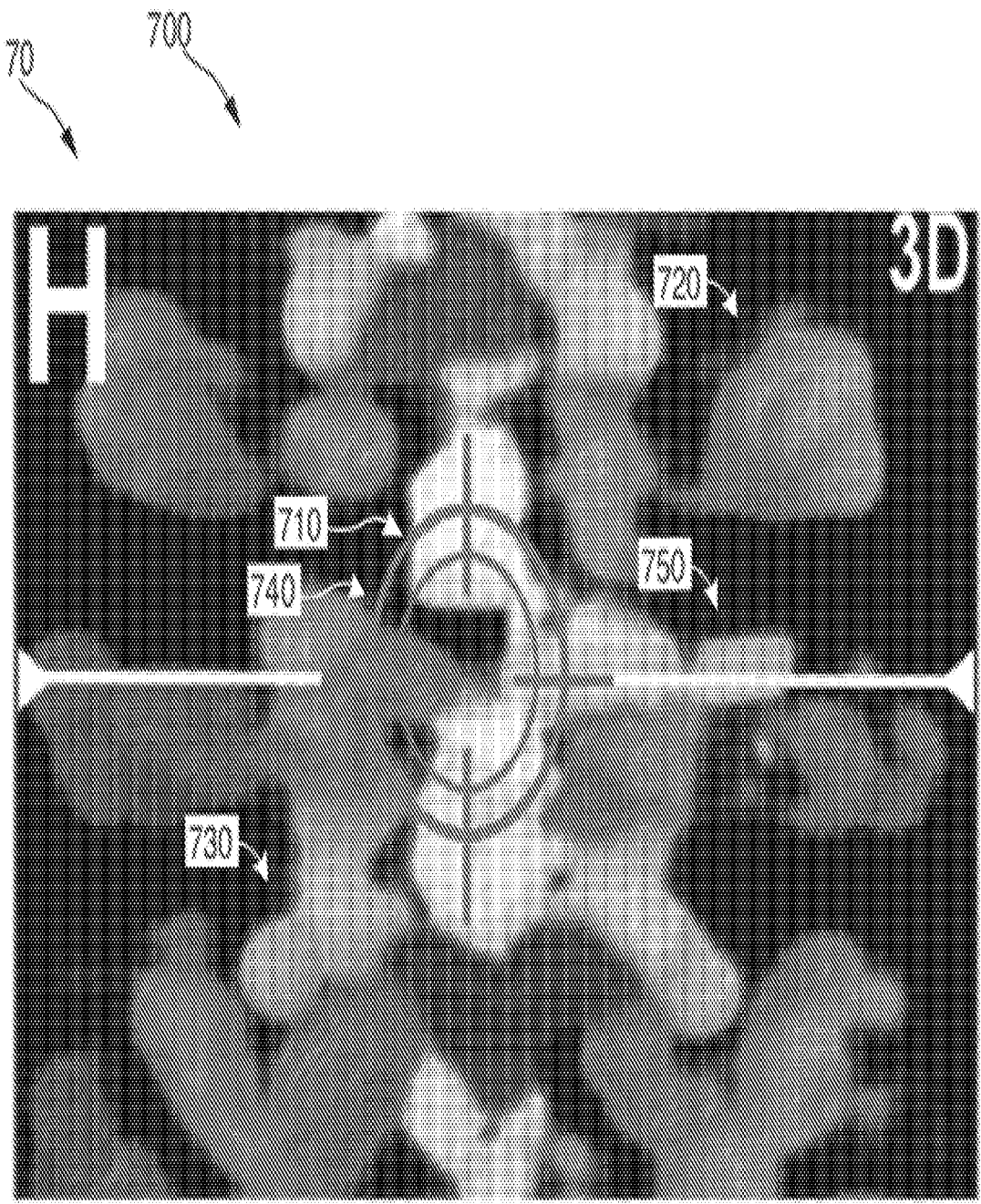
FIG. 7 illustrates an example of a three-dimensional display of spinal anatomy along the posteroanterior line-of-sight.

FIG. 7 illustrates an example of a three-dimensional display 70 of spinal anatomy 700 along the posteroanterior line-of-sight. In the illustrated display 70, the third dimension corresponds to the depth of the bone surface from the patient's skin. The depth of the bone surface from the patient's skin is illustrated in two-dimensional display 70 by the color of the bone surface. For example, this depth is illustrated as progressing from lighter in color (closer to the skin surface) in bone surface 710 to darker in color (further from the skin surface) in bone surface 720. Bone surface 730 has a middle color, which indicates that it is located at a depth between bon surfaces 710 and 720. In addition, display 70 illustrates optional crosshairs 740 that indicate an automatically-detected therapy site and an optional automatically-detected therapy applicator 750, which can be the same as therapy applicator 116.

The composite image produced in step 218 can be rendered in step 234 either as a set of surfaces (meshes, polygons, etc. as desired) with optional transparency, or as a point cloud with variable point size and transparency as desired). External optional lighting and other effects may be applied as desired. The 3D fitted model produced in step 230 is most simply rendered in step 234 as a series of 3D objects in space, with surface textures depending on each of the 3D object's properties and user significance.

In addition, in step 218 the user annotations from step 232 can be displayed with the rendered composite image and/or with the rendered 3D fitted model as points, objects, areas, lines, or volumes in 3D space co-registered with the other items in space.

In step 238 (via placeholder A in flow chart 20), analytics on the 3D image and/or model are computed. In this step, the parameters of the 3D model (from step 230), the 3D composite image (from step 218) and/or the user annotations (from step 232) are analyzed to produce useful information for one or more purposes. For example, the computed analytics can be used to help diagnose a disease state, progression of disease, or other health metric that can be inferred from one or more of the inputs (e.g., outputs from steps 230, 218, and/or 232). Examples of such analytics include vertebral dimensions, inter-vertebral distance, inter-vertebral rotation, measures of spinal scoliosis, scoliosis progression over time, and other disease or health markers.

In another example, the computed analytics can be used to help with the planning and/or guidance of a therapeutic process, such as a needle insertion or energy-based therapy. Examples of such analytics include measurement of the clearance a needle inserted into a given inter-vertebral space will have from the nearest bone surface (e.g., which can indicate the difficulty of neuraxial anesthesia introduction in that location), identification of an appropriate needle insertion site and track/trajectory (line), or identification of the depth of certain anatomical features from the skin (e.g., epidural space).

In yet another example, the computed analytics can be used for real-time guidance in 3D space. Examples of such real-time guidance include giving the user feedback on such data as proximity to fiducial markers, annotations and/or 3D model locations such as spinal midline, and relative angle of an external object (e.g., therapy applicator 116) to, for example, an appropriate needle insertion track.

In step 242 (via placeholder A in flow chart 20), the locations of the 3D structure that require additional scan information are determined and/or identified. In this step, the current state of the 3D composite image of step 218 and/or all or part of the 3D model from step 230 are used to estimate to which degree different parts of the 3D space corresponding to the anatomy-of-interest have been adequately sampled by the ultrasound beam (from ultrasound probe 104). If the ultrasound beam is moved quickly across a region of the target anatomy, then based on the known spatial resolution of the imaging system, there may not be sufficient sampling of the region to meet Nyquist sampling, or to ensure sufficient oversampling, and/or to provide a signal-to-noise ratio that is adequate for subsequent processing.

Figure 3:
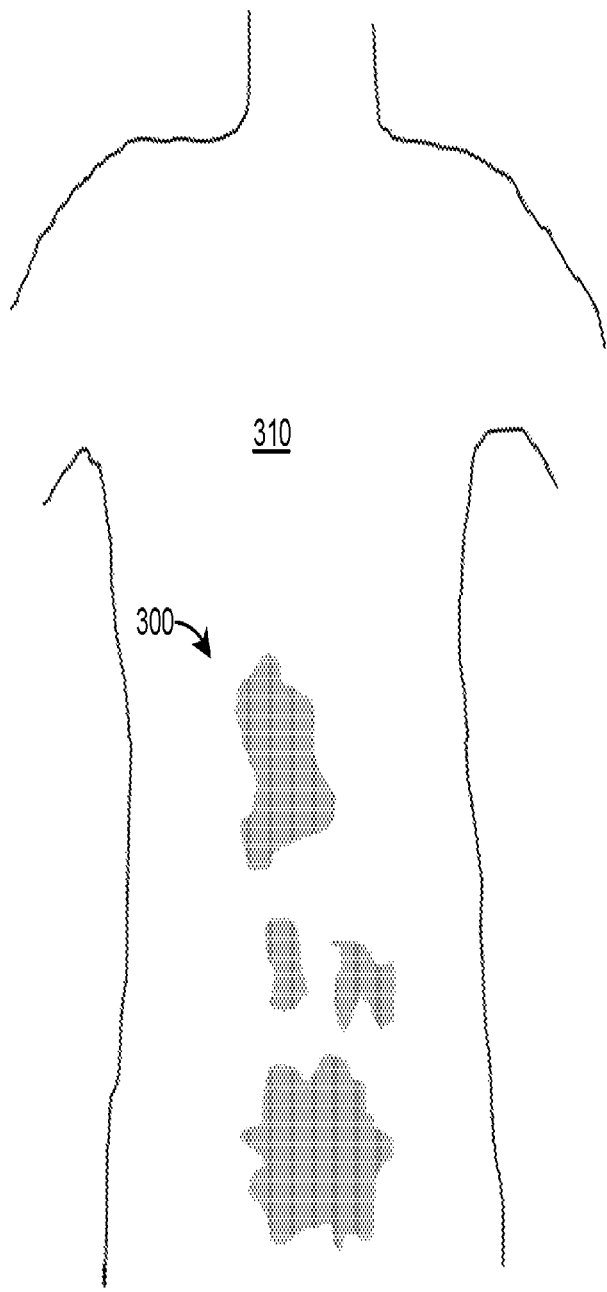
FIG. 3 is a representative illustration of a display that graphically identifies areas in a human subject that have not been sufficiently scanned with an ultrasound probe.

In one example, step 242 can be performed by maintaining a volume density function over 3D space, and filling the volume density in additively as an ultrasound plane or volume passes through it. The current state of the volume density can be indicated interactively to the user (e.g., graphically, by voice, etc.). The current state of the volume can include where there is sufficient sampling or where there is not sufficiently sampled. There are many ways to determine sufficient volumetric sampling. One method is to assert a minimum sampling of 3D ultrasound pixels per volume, for example 25 pixels per cubic centimeter or other volume cell. Other, more intelligent sampling metrics could include continuity with existing adequately-sampled volumes (e.g., showing a gap but not limited volumetric extent), or use a volumetric sampling threshold that is adaptive depending on position and upon such variables as bone surface density, information (e.g., entropy) content or data statistics in the volume cell, and estimates of what kind of anatomy the volume cell contains. This can be used to let the user "paint in" the missing areas or "wipe away" the areas of under-sampling by indicating where scanning or additional scanning is needed, respectively. This approach is illustrated in FIG. 3, which is a representative illustration of a display that graphically identifies under-sampled areas 300 in a human subject 310 that have not been sufficiently scanned with an ultrasound probe. When the ultrasound probe 104 acquires sufficient data for the under-sampled areas 300, the under-sampled areas 300 are removed from the display.

In addition or in the alternative, step 242 can be performed by providing the user with a visual indicator where to move the ultrasound probe 104 in order to maximize sampling productivity—e.g., move left, up, down, etc. from the current location. Sampling productivity is defined as the amount of volume that can be adequately sampled in a unit of time.

In addition or in the alternative, step 242 can be performed by using volume density (e.g., by maintaining a volume density function over 3D space as discussed above) or some other sampling state indicator to provide a real-time 3D rendering to the user which has a level of detail that indicates sampling progress. This can be achieved by making under-sampled areas blurry, while adequately-sampled areas can be higher resolution, or alternatively by using color coding or some other visual indication to help the user fill in the sample space.

In addition or in the alternative, step 242 can be performed by providing feedback on sampling progress to the user by way of the 3D model display. For example, vertebrae that are under-sampled can have a different appearance (color, resolution, etc.) than adequately-sampled vertebrae, thereby guiding the user to acquire more data on the under-sampled vertebrae.

In step 246, the 3D position of therapy applicator 116 is tracked. This step is the same as or substantially the same as step 204, except the tracked object is a therapy applicator, for example a needle guide or an object that is capable of directing energy towards a target (e.g., RF ablator, high intensity focused ultrasound (i.e., HIFU) element). The object tracking system 112 can be used to track the 3D position and orientation of therapy applicator 116.

In step 250, the desired therapy application site relative to 3D image structure is input by the user (e.g., via a user interface such as a mouse, a touch screen, a keyboard, or other user interface). Once the 3D composite image (step 218), 3D model fit (step 230), analytics (step 232), and/or user annotations (step 138) have been produced, the user can indicate positions, lines, areas, and/or volumes where the therapy should be applied. Some examples of methods to indicate where to apply therapy include: (1) point target, area, or small volume to indicate a needle tip target; (2) point target, area, or small volume to indicate a needle insertion point target; (3) a line that describes the point, angle-of-insertion of a needle, and/or final needle tip target; and/or (4) volume or area where anesthesia or energy therapy should be applied.

In step 254, a combination of one or more of the following is displayed to the user (e.g., on display 140 and/or on optional therapy applicator display 118 (which is disposed on or integrated into the optional therapy applicator 116)): the human subject (or portion thereof such as the relevant anatomical region), the device operator (or portion thereof such as the operator's arm or hand), the ultrasound transducer/probe 104 (or portion thereof such as the tip of ultrasound probe 104), current (e.g., instantaneously-acquired) ultrasound image frame(s), a 2D fluoroscopy-like bone structure image, a 2D or 3D depth-encoded composite bone structure image, a 3D composite bone structure image, 3D model of bone structure, locations of bone structure that require additional scan data, computed analytics from 3D image or model, the current position of therapy applicator, directional indications for navigation of therapy applicator to desired location, a depiction of the potential therapy field, fiducial markers, and/or user annotations.

If an appropriate therapy application track has been previously designated, this can be shown as a directional indicator for navigation of therapy, for example as graphics showing a line segment for the appropriate needle track, skin entry point, and/or final needle target point, along with analytics such as needle angle error (azimuthal and/or elevational), distance needle tip is to target tip location, and/or projected effective area of therapeutic agent (e.g., anesthesia, directed energy application, etc.). The current target track for the therapy applicator can also be shown with the intent that the two line segments (e.g., appropriate needle track and current target track) should eventually match. The area of bone or other anatomy that the current therapy applicator will intersect with can also be highlighted in real time. An example of this display is illustrated in FIG. 7.

In some embodiments, the display can display a co-alignment of (a) the current or instantaneously-acquired two-dimensional ultrasound image frame and (b) the potential therapy field for the therapy applicator at its current position and current orientation.

The current ultrasound image frame, for example a 2D image with optional bone enhancement, can be displayed in the 3D image in the correct orientation and plane of the ultrasound scan plane, or alternatively as a flat image at an arbitrary, user-settable location in the 3D scene, in all cases with arbitrary and/or customizable transparency. The therapy applicator 116 (e.g., needle, RF ablation needle), if it intersects the 2D ultrasound image, can be specifically detected and rendered in the correct orientation with respect to the 3D volume and the ultrasound plane. Further, if an injectate is expelled from the needle and if the 2D ultrasound plane intersects the path of the injectate, then this injectate can be detected and rendered in the correct orientation with respect to the 3D volume and the ultrasound plane. If an energy therapy device (e.g., RF ablation or HIFU) is used rather than a needle, the energy field of the device can be similarly rendered (e.g., expected spatial extent of energy effect). The potential therapy field can include the expected path of the injectate and the expected spatial extent of energy effect from an energy therapy device. The locations that require additional scan data (as in step 242) can be shown in their actual locations in the 3D field, in particular if a virtual reality headset is used, the areas needing extra scanning can be shown intuitively as an augmented display overlaid upon the actual images of the human subject.

If the ultrasound probe has a display attached (e.g., optional probe display 108), and/or if the optional therapy applicator has a display attached (e.g., optional therapy applicator display 118), either or both of these screens can be used to display any of the 2D and/or 3D data, described above, in real time (e.g., instantaneously acquired), alone or in addition to an external 2D or virtual reality display. The attached display can also be used to display information related to the relative location of the ultrasound probe 104 and the target location(s). If a virtual reality headset is used, one or more virtual 2D displays can be produced in the 3D VR space, these can be placed relative to the headset, and/or the probe, or statically in 3D space.

Figure 8:
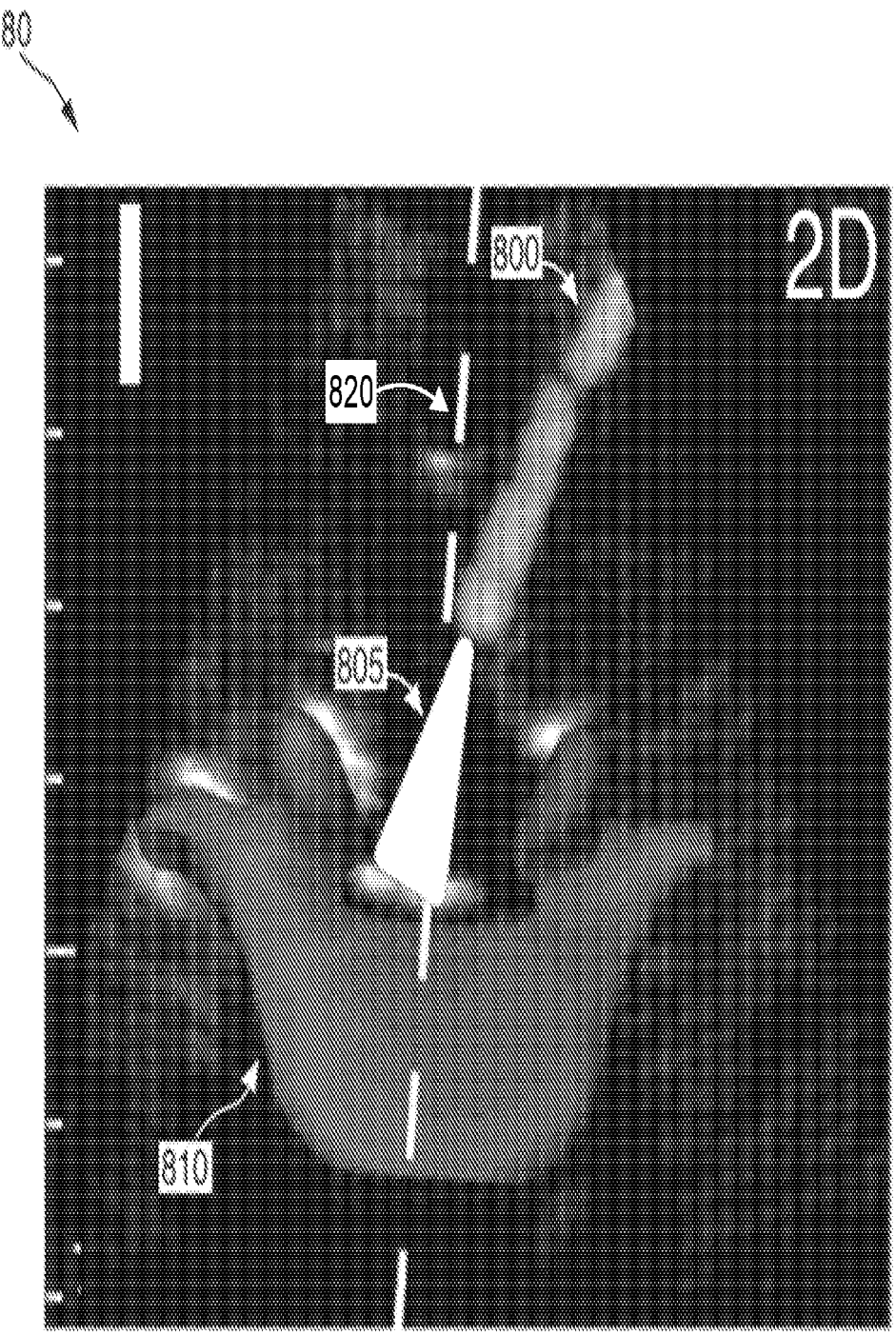
FIG. 8 illustrates a two-dimensional display of an alignment of a potential therapy field with a therapy site.

FIG. 8 is a two-dimensional display 80 of an alignment of a potential therapy field with a therapy site. In display 80, an automatically-detected therapy applicator 800 is illustrated as extending towards a target anatomical feature 810 (e.g., a bone surface, an organ, etc.). Using aspects of the invention described herein, the system automatically determines the position and orientation of the therapy applicator 800 (e.g., using object tracking system 112) and the three-dimensional locations of the bone anatomy (e.g., as discussed above with respect to flow chart 20) such as spine midline 820, which can function as an anatomical reference plane (i.e., the spinal midline 820 does not exist as part of the physical anatomy, but rather is an imaginary line that servers as a reference with respect to physical anatomical features). When the potential therapy field 805 of therapy applicator 800 is aligned with the target anatomical feature 810, as illustrated in FIG. 8, the system can provide a visual and/or audible indication of such alignment (e.g., by changing the color of the target anatomical feature 810, flashing a light, generating a sound, etc.).

Example A—Guidance of Epidural Anesthesia Procedure

In this example, the goal is to guide a Tuohy needle into the epidural space in the lumbar spine of a patient, for catheter placement to provide long-lasting anesthesia. The current standard of care is to palpate spinal anatomy to identify an inter-vertebral space and insert the needle followed by the "loss of resistance" technique, where a syringe is used to sense the reduced pressure when the needle reaches the target epidural space. To achieve improved accuracy for this procedure, the user can scan the patient using an ultrasound probe 104 with attached screen 108, while the probe is tracked by object tracking system 112. As the user scans, a bone-enhanced (step 214) 3D composite image is compiled (step 218), an interim 3D model fit (step 230) and an indication of scan density sufficiency is calculated (step 242), all these shown in 3D (step 254) on display 140 (e.g., a laptop display, an external display, a virtual reality headset, etc.) and/or on optional probe display 108 in real time. The scan density indication uses a color code, highlighting the target anatomy in a degree of blue (or other color) to show when scans in an area are of sufficient density.

Optionally one or more fiducials 124 can be created and tracked (step 226), for example by a user interface interaction on the ultrasound probe when the probe tip is coincident with left and right pelvic extremities, and/or the bony protrusion above the intra-gluteal cleft. These fiducials 124 will be added to the combined image (step 254) on display 140 and/or on optional therapy applicator display 118.

Figure 4:
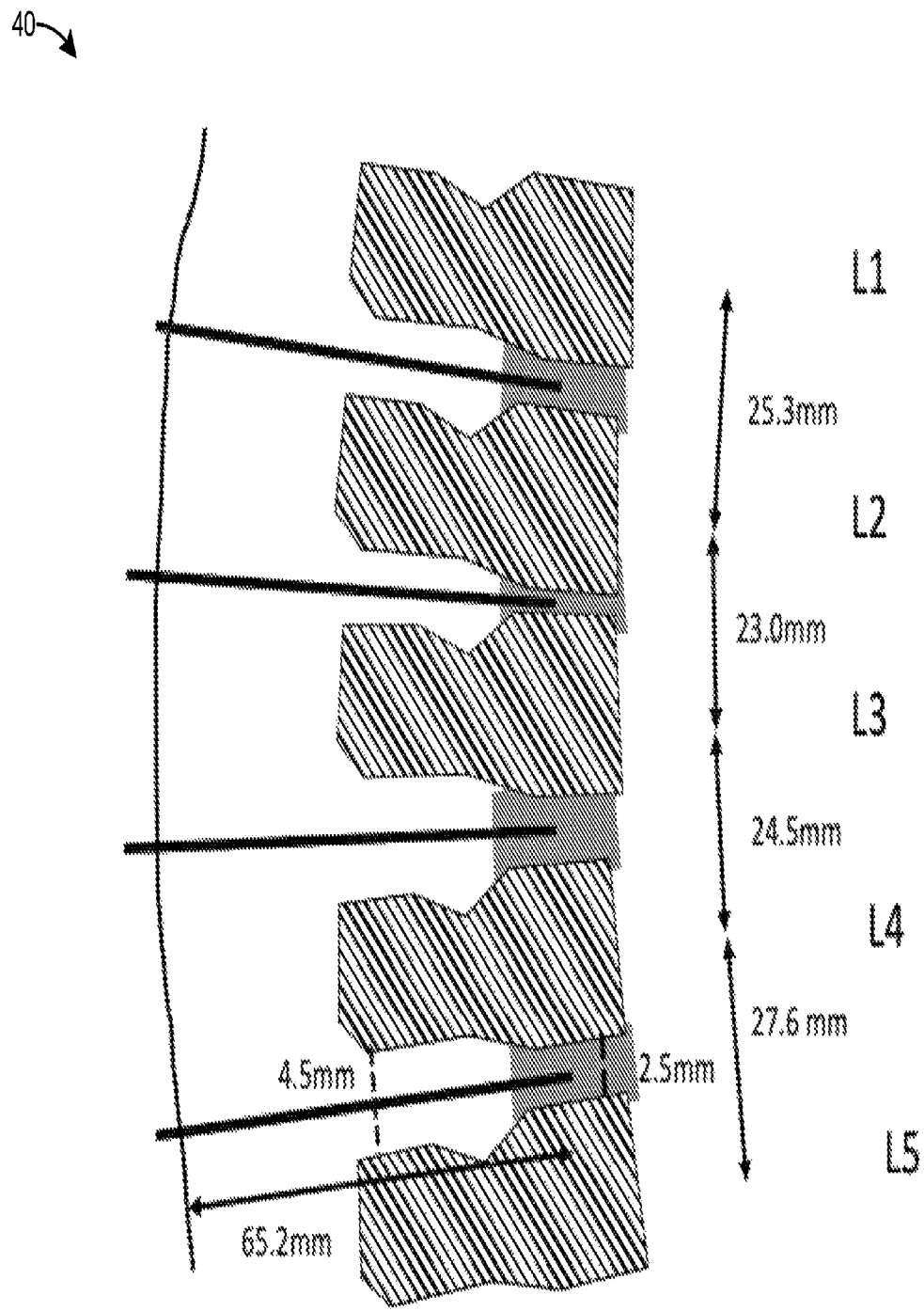
FIG. 4 is a display of an example 3D spine model or example 3D spine data with analytics overlaid spine analytics based on a 3D spine model, for guiding epidural injections.

Once a sufficient level of scan density has been achieved over the target anatomy (e.g., lumbar spine), the 3D model fit (step 230) can identify the lumbar vertebra, with intervertebral spaces highlighted along with analytics (step 238) based on the 3D fit such as intervertebral space dimensions, appropriate needle track to epidural space at each candidate lumbar intervertebral space, depth to epidural space and minimum clearance to a bony surface for each needle track. FIG. 4 is a display 40 of an example 3D spine model or example 3D spine data with analytics overlaid spine analytics based on a 3D spine model, for guiding epidural injections. Though the display 40 is illustrated in two dimensions, it is noted that the display 40 can also illustrate the same information in three dimensions.

Figure 5:
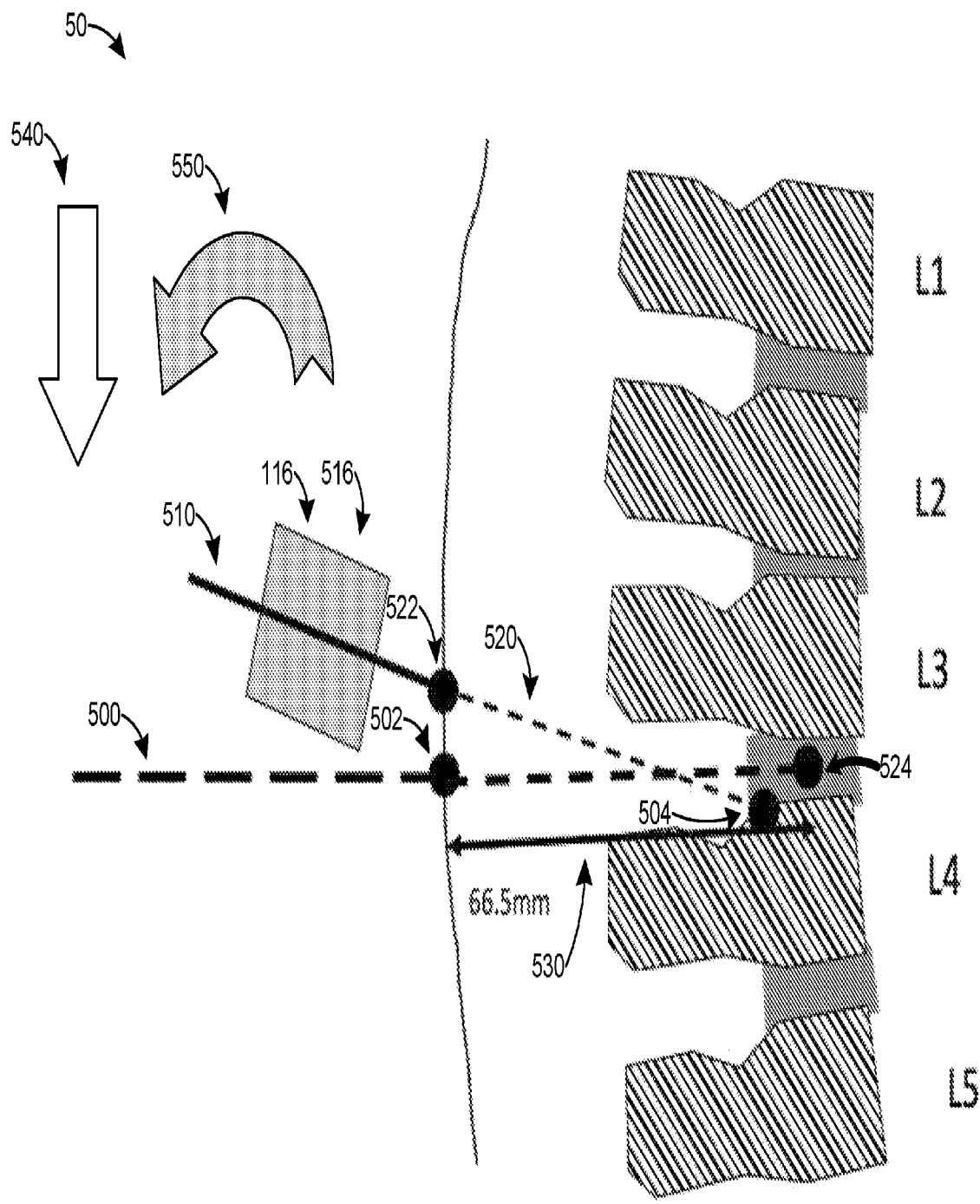
FIG. 5 illustrates a display for guiding a needle along an appropriate needle track according to one or more embodiments.

FIG. 5 illustrates a display 50 for guiding a needle along an appropriate, satisfactory, user-selected, or automatically-selected needle track 500 (collectively, "appropriate needle track") according to one or more embodiments. In some embodiments, the appropriate needle track 500 is a subsequent and/or future needle track required to deliver therapy to the target therapy site. The user can identify the appropriate needle track 500 using the display 140 and/or optional therapy applicator display 118 and analytics specific to this procedure (e.g., analytics illustrated in FIG. 4). For example, at the current therapy applicator 116 position, analytics can be displayed such as the vertebra it is over (e.g. L1-L5), lateral distance to spinal midline, and/or epidural space depth 530. Though the display 50 is illustrated in two dimensions, it is noted that the display 50 can also illustrate the same information in three dimensions.

Once the appropriate needle track 500 has been identified, a tracked therapy applicator 116 (tracked in step 246) can be used to guide the needle 510 to the desired appropriate needle track 500. As the therapy applicator 116 (in this case, a tracked needle guide 516) is moved, the current (or projected) needle track 520 can be displayed on the display 50 (which can include display 140 and/or on optional therapy applicator display 118) (in step 254) including the current skin entry point 522 and the current (or projected) needle end point 524. The display 50 also illustrates the appropriate needle track 500 including the appropriate skin entry point 502 and the appropriate needle end point 504. Displaying these data and images can assist the operator with moving and/or orienting the therapy applicator 116 so the appropriate needle track 500 is realized. In some embodiments, the display 50 can include an arrow that indicates the direction to translate and/or rotate the therapy applicator 116 to align the current needle track 520 with the appropriate needle track 500. For example, the display 50 can include a first arrow 540 that indicates a direction to translate the therapy applicator 116 to achieve the appropriate needle track 500 and a second arrow 550 that indicates a direction to rotate the therapy applicator 116 to achieve the appropriate needle track 500. Each arrow 540, 550 can be colored or displayed differently to avoid confusion to the user. Additional or fewer arrows can be provided (e.g., based on the number of dimensions in which the current needle track 520 is misaligned with the appropriate needle track 500). An example of system and method for angularly aligning a probe with a target probe angle is disclosed in U.S. patent application Ser. No. 15/864,395, titled "System and Method for Angular Alignment of a Probe at a Target Location," filed on Jan. 8, 2018, which is hereby incorporated by reference.

At this point, the conventional loss-of-resistance technique can be used for needle insertion. Optionally, if mechanically possible the therapy applicator 116 can track the remote end of the needle and thus track needle insertion depth in real-time, with visual and/or audible feedback from the laptop. The therapy applicator 116 can track the needle end in several ways. One way is to calculate the needle tip position using geometry, if the therapy applicator 116 position and orientation are known, and the needle is stiff (does not bend).

Optionally, a virtual reality headset can be used, during some or all parts of the procedure, as display 140 (or in addition to display 140). During 3D scan development, the headset camera can be used to show the probe and patient, along with the ultrasound image plane and other aspects of step 254. During therapy application, the user can use the VR headset to view the projected and appropriate needle tracks from any angle by moving their head around therapy applicator 116. Various virtual heads-up displays can be placed around the scene to provide any kind of procedure feedback desired.

It is noted that the ultrasound probe 104 and/or therapy applicator 116 can be positioned via a machine, such as a robotic actuator, based on direct input from a user or algorithmically based on the information provided herein. For example, a robot, instead of a human user, can automatically move the therapy applicator 116 to the location considered appropriate for reaching the desired target based on the outputs from this technology.

Example B—Spinal Anatomy Analysis for Disease State Assessment

In this example, the goal is to scan a patient to build up a 3D model of his/her spinal anatomy in order to visualize it without requiring ionizing radiation (e.g., X-ray, CT scan, etc.) or an expensive procedure (e.g., MRI). A 3D spine model can be used to extract analytics and assess the presence or extent of disease states. One example use of this technique is to diagnose or track the progression of juvenile scoliosis. The main current tool for this kind of diagnosis is X-ray imaging. However, it is undesirable to expose children to repeated X-rays, and first-line care providers may not have easy access to an X-ray machine and instead use other methods with limited accuracy (e.g., measuring external spine angulation). Therefore, an inexpensive accurate spinal analysis system as described in this example would be an improvement over the current standard of care.

To build a 3D spinal anatomy model in this embodiment, the main processing unit 136 (e.g., a computer such as a laptop) would direct the user to move the ultrasound probe 104 to the sacrum and begin scanning in bone enhancement mode (step 214) there. While scanning, the user would see a 3D composite image (step 218) and 3D interim model (step 230) build up on the display 140 (e.g., the computer/laptop display) and/or on optional probe display 108 in real time, along with an indication of scan density sufficiency (step 242). Once sufficient scan density has been built up in the vicinity of the sacrum, the computer would direct the user to move up to the lowest vertebra, L5 and scan that. Again, once sufficient scan density has been built up, the user would be directed to the next vertebra up, L4, and so on, until a certain number of vertebra has been scanned satisfactorily.

At this point, the 3D composite image (step 218) should be sufficient for a full spinal 3D model (step 230) to be developed, along with analytics relevant to the spine (step 238). The analytics related to a full spine model could include relative vertebral positions, intervertebral spacing, measures of spinal curvature in one or more axes. In addition, incorporation of data from previous scans over time could be included, to show the progression of spinal changes and disease state over time.

Now, the display 140 and/or optional probe display 108 can be used to show the combined spine model in 3D space, along with analytics derived from it, and optionally to show animations including models from prior scans, and/or development of analytically-derived measures that have changed over time.

If a virtual reality headset is available, this can be used during any or all stages of this example (e.g., as display 140 or in addition to display 140). First, during scanning, the headset can use the front-facing camera 130 to let the user see the patient's back during scanning, in addition to the composite 3D image (step 218), 3D model (step 230) and other parts of the 3D display listed in and/or discussed above with respect to step 254. During this phase, the virtual reality display can also highlight the vertebrae that have already been scanned, and likely locations for the next vertebra to scan, and guide the scan progression in other ways. Once the scan is complete, the user can view the full 3D display (displayed in step 254) from any angle, with the anatomy shown "inside" the patient, by walking around the patient. In addition, the patient can view what the user sees, and/or after the scan view the spine scan in a virtual reality environment along with other prior scans, including animations over time and/or annotations of analytical information.

This general method of diagnosing disease state related to 3D analysis of bony anatomy can be extended by performing two or more scans, whereby for subsequent scans the patient is requested to go through some range of motion (e.g., back extension or hunching forward). The two or more scans can be used to evaluate the range of motion that bony anatomy is capable of, and can be used as part of a historical record to assess disease state progression and/or provide feedback on the effect of various therapies.

Example C—Recording Bony Anatomy in 3D in Standard Format for Later Review

In this example, the goal is to scan a patient to build up a 3D model of bony and other anatomy, and to save this scan information for later review, possibly by a different person and possibly at a different location. This approach has the benefit that a technician can obtain the anatomy model by scanning a patient, whereas one or more highly skilled medical professionals could later interpret the model data interactively at any location. If the anatomy model data is stored in a standard volumetric, surface, or other format, for example those provided by the Digital Imaging and Communications in Medicine (DICOM) standard (available at http://www.dicomstandard.org/), then any consumer of the data can use existing or new tools to explore the data, transmit it, and store it, for example using PACS systems (picture archiving and transmission systems).

As the data set is intrinsically 3D in nature, a virtual reality system could easily be used to navigate the data, control analytics and display, and annotate the data. Alternatively, non-VR tools can be used to explore and annotate the data. In one possible variation, multiple users could view, annotate, and control the displayed 3D data in real time, using networked communication for collaborative medical analysis. This example is analogous to the workflow of echo-cardiology ultrasound, where a sonographer collects a large volume of data from a cardio scan, and the cardiologist later inspects this using a PACS system and standard tools. In the same way, a technician could use an ultrasound system with bone enhancement technology and 3D position tracking as described in this disclosure, to obtain 3D anatomy models from a patient, then an orthopedic or other medical specialist could analyze and inspect the data using a PACS system.

Examples of Illustrative Embodiments

Example 1. An ultrasound imaging and therapy guidance system comprising: an ultrasound probe that generates a positionally-adjusted ultrasound beam to acquire three-dimensional image data of bone anatomy in a human subject; an object tracker configured to detect a current position and a current orientation of the ultrasound probe; a therapy applicator to deliver a therapy to the human subject; a mechanical apparatus coupled to the ultrasound probe and the therapy applicator to set a predetermined relative position of the therapy applicator with respect to the ultrasound probe; a processor; a non-transitory computer memory operatively coupled to the processor. The non-transitory memory comprises computer-readable instructions that cause the processor to: detect a position and an orientation of three-dimensional bone surface locations based at least in part on the three-dimensional image data and the current position and the current orientation of the ultrasound probe; automatically detect a target therapy site relative to the three-dimensional bone surface locations; determine an appropriate position and an appropriate orientation of the therapy applicator required to deliver the therapy to the target therapy site; and generate display data. The system further includes a display in electrical communication with the processor, the display generating images based on the display data, the images comprising: an indication of the three-dimensional bone surface locations; an instantaneously-acquired two-dimensional ultrasound image frame that is co-aligned with a potential therapy field for the therapy applicator at a current position and a current orientation of the therapy applicator; an indication of the target therapy site relative to the three-dimensional bone surface locations; and graphical indicators that indicate whether the target therapy site and potential therapy field are aligned.

Example 2. The system of example 1, wherein the computer-readable instructions further cause the processor to automatically detect the target therapy site relative to the three dimensional bone surface locations using a neural network.

Example 3. The system of Example 1 or 2, wherein the computer-readable instructions further cause the processor to detect the position and the orientation of the three-dimensional bone surface locations by fitting the three-dimensional image data to a three-dimensional bone model.

Example 4. The system of any of Examples 1-3, wherein the images generated by the display further include bone landmark locations.

Example 5. The system of any of Examples 1-4, wherein the computer-readable instructions further cause the processor to automatically detect the target therapy site using the three-dimensional bone model.

Example 6. The system of any of Examples 1-4, wherein the indication of the three-dimensional bone surface locations are displayed as two-dimensional bone surface images with a third dimension encoded to represent a bone surface location along the third dimension.

Example 7. The system of Example 6, wherein the third dimension is graphically encoded to represent the bone surface location along the third dimension.

Example 8. The system of Examples 6 or 7, wherein the third dimension is color encoded to represent the bone surface location along the third dimension.

Example 9. The system of any of Examples 1-8, wherein the appropriate position and the appropriate orientation of the therapy applicator are determined based at least in part on the predetermined relative position of the therapy applicator with respect to the ultrasound probe.

Example 10. The system of any of Examples 1-9, wherein: the object tracker is configured to detect the current position and the current orientation of the therapy applicator, and the appropriate position and the appropriate orientation of the therapy applicator are determined based at least in part on the current position and the current orientation of the therapy applicator.

Example 11. The system of any of Examples 1-10, wherein the images generated by the display further include a current position and a current orientation of the potential therapy field.

Example 12. The system of any of Examples 1-11, wherein the images generated by the display further include the current position and the current orientation of the therapy applicator.

Example 13. The system of any of Examples 1-12, wherein the images generated by the display further include dimensional and orientation information of the bone anatomy calculated from the three-dimensional bone surface locations.

Example 14. The system of any of Examples 1-13, wherein the therapy applicator comprises a needle guide, a needle, an ablation instrument, and/or a high-intensity focused ultrasound transducer.

Example 15. The system of any of Examples 1-14, wherein the target therapy site includes an epidural space, an intrathecal space, or a medial branch nerve.

Example 16. The system of any of Examples 1-15, wherein the ultrasound probe is configured to be positionally adjusted manually by a user.

Example 17. The system of any of Examples 1-16, wherein the ultrasound probe is configured to be positionally adjusted automatically with a mechanical motorized mechanism.

Example 18. The system of any of Examples 1-17, wherein the object tracker includes inductive proximity sensors.

Example 19. The system of any of Examples 1-18, wherein the object tracker includes an ultrasound image processing circuit.

Example 20. The system of Example 19, wherein the ultrasound image processing circuit is configured to determine a relative change in the current position of the ultrasound probe by comparing sequentially-acquired ultrasound images of the three-dimensional image data.

Example 21. The system of any of Examples 1-20, wherein the object tracker includes optical sensors.

Example 22. The system of Example 21, wherein the optical sensors include fixed optical transmitters and swept lasers detected by the optical sensors, the optical sensors disposed on the ultrasound probe.

Example 23. The system of any of Examples 1-22, wherein the object tracker includes integrated positioning sensors.

Example 24. The system of Example 23, wherein the integrated positioning sensors include an electromechanical potentiometer, a linear variable differential transformer, an inductive proximity sensors, rotary encoder, an incremental encoder, an accelerometer, and/or a gyroscope.

Example 25. The system of any of Examples 1-25, wherein the three-dimensional bone surface locations include three-dimensional spine bone locations.

Example 26. The system of any of Examples 1-26, wherein the positionally-adjusted ultrasound beam is positionally adjusted by mechanically movement of the ultrasound probe and/or electrical steering of the positionally-adjusted ultrasound beam.

Example 27. A method for guiding a therapy applicator, comprising: positionally adjusting an ultrasound beam, generated by an ultrasound probe, on a human subject to acquire three-dimensional image data of bone anatomy in the human subject; detecting, with an object tracker, a current position and a current orientation of the ultrasound probe while positionally adjusting the ultrasound beam; determining a position and an orientation of three-dimensional bone surface locations based at least in part on the three-dimensional image data and the current position and the current orientation of the ultrasound probe; automatically detecting a target therapy site relative to the three-dimensional bone surface locations; determining an appropriate position and an appropriate orientation of the therapy applicator required to deliver a therapy to the target therapy site; displaying images on a display that is in electrical communication with the computer, the images comprising: an indication of the three-dimensional bone surface locations; an instantaneously-acquired two-dimensional ultrasound image frame that is co-aligned with a potential therapy field for the therapy applicator at a current position and a current orientation of the therapy applicator; an indication of the target therapy site relative to the three-dimensional bone surface locations; and graphical indicators that indicate whether the target therapy site and potential therapy field are aligned.

Example 28. The method of Example 27, further comprising using a neural network in a computer to automatically detect the target therapy site relative to the three dimensional bone surface locations.

Example 29. The method of Example 27 or 28, further comprising fitting the three-dimensional image data to a three-dimensional bone model.

Example 30. The method of Example 29, further comprising determining the position and the orientation of the three-dimensional bone surface using the three-dimensional bone model.

Example 31. The method of Example 29 or 30, further comprising identifying bone landmark locations using the three-dimensional bone model.

Example 32. The method of Example 31, wherein the images comprise the bone landmark locations.

Example 33. The method of any of Examples 30-32, further comprising automatically detecting the target therapy site using the three-dimensional bone model.

Example 34. The method of any of Examples 27-33, wherein the indication of the three-dimensional bone surface locations are displayed as two-dimensional bone surface images with a third dimension encoded to represent a bone surface location along the third dimension.

Example 35. The method of Example 34, further comprising graphically encoding the third dimension to represent the bone surface location along the third dimension.

Example 36. The method of Example 34 or 35, further comprising color encoding the third dimension to represent the bone surface location along the third dimension.

Example 37. The method of any of Examples 27-36, further comprising mechanically coupling a mechanical apparatus coupled to the ultrasound probe and the therapy applicator, the mechanically apparatus setting a predetermined relative position of the therapy applicator with respect to the ultrasound probe.

Example 38. The method of Example 37, further comprising determining the appropriate position and the appropriate orientation of the therapy applicator based at least in part on the predetermined relative position of the therapy applicator with respect to the ultrasound probe.

Example 39. The method of any of Examples 27-38, further comprising: detecting, with the object tracker, the current position and the current orientation of the therapy applicator; and determining the appropriate position and the appropriate orientation of the therapy applicator based at least in part on the current position and the current orientation of the therapy applicator.

Example 40. The method of any of Examples 27-39, wherein the images further include a current position and a current orientation of the potential therapy field.

Example 41. The method of any of Examples 27-40, wherein the images further include the current position and the current orientation of the therapy applicator.

Example 42. The method of any of Examples 27-41, wherein the images further include dimensional and orientation information of the bone anatomy calculated from the three-dimensional bone surface locations.

Example 43. The method of any of Examples 27-42, wherein the therapy applicator comprises a needle guide, a needle, an ablation instrument, and/or a high-intensity focused ultrasound transducer.

Example 44. The method of any of Examples 27-43, wherein the target therapy site includes an epidural space, an intrathecal space, or a medial branch nerve.

Example 45. The method of any of Examples 27-44, wherein positionally adjusting the ultrasound beam comprises mechanically moving the ultrasound probe.

Example 46. The method of any of Examples 27-45, further comprising positionally adjusting the ultrasound probe with a mechanical motorized mechanism.

Example 47. The method of any of Examples 27-46, wherein positionally adjusting the ultrasound beam comprises electronically scanning the ultrasound beam.

Example 48. The method of any of Examples 27-47, wherein the object tracker includes inductive proximity sensors.

Example 49. The method of any of Examples 27-48, wherein the object tracker includes an ultrasound image processing circuit.

Example 50. The method of Example 49, further comprising, with the ultrasound image processing circuit, determining a relative change in the current position of the ultrasound probe by comparing sequentially-acquired ultrasound images of the three-dimensional image data.

Example 51. The method of any of Examples 27-50, wherein the object tracker includes optical sensors.

Example 52. The method of Example 51, wherein the optical sensors include fixed optical transmitters and swept lasers detected by the optical sensors, the optical sensors disposed on the ultrasound probe.

Example 53. The method of any of Examples 27-52, wherein the object tracker includes integrated positioning sensors.

Example 54. The method of Example 53, wherein the integrated positioning sensors include an electromechanical potentiometer, a linear variable differential transformer, an inductive proximity sensors, rotary encoder, an incremental encoder, an accelerometer, and/or a gyroscope.

Example 55. The method of any of Examples 27-54, wherein the three-dimensional bone surface locations include three-dimensional spine bone locations.

Example 56. The method of any of Examples 27-55, wherein the current position and the current orientation of the ultrasound probe are detected using an object tracker.

Example 57. The method of any of Examples 27-56, further comprising: acquiring two-dimensional ultrasound image data of the bone anatomy at a plurality of ultrasound probe locations; and combining the two-dimensional ultrasound image data and the ultrasound probe locations to form the three-dimensional image data.

Example 58. The method of any of Examples 27-57, wherein the two-dimensional image data includes pixels and the method further comprises determining a three-dimensional position of each pixel based on the ultrasound probe locations.

Example 59. The method of any of Examples 27-58, further comprising performing bone enhancement processing to enhance any bones and/or bony features in the ultrasound images.

Example 60. The method of any of Examples 27-60, further comprising: receiving a user-interface event; and recording a fiducial position of the ultrasound probe based on a time that the user-interface event is received.

These non-limiting examples can be combined in any combination or permutation.

Having thus described several aspects and embodiments of the invention, it is to be appreciated that various alterations, modifications, and improvements will readily occur to those of ordinary skill in the art. Such alterations, modifications, and improvements are intended to be within the spirit and scope of the invention described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will appreciate the many equivalents to the specific embodiments described herein. It is, therefore, to be understood that the foregoing embodiments are presented by way of example only and that inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in numerous ways. One or more aspects and embodiments of the present application involving the performance of processes or methods may utilize program instructions executable by a device (e.g., a computer, a hardware processor, or other device) to perform, or control performance of, the processes or methods.

In this respect, various inventive concepts may be embodied as a non-transitory computer memory and/or a non-transitory computer readable storage medium (or multiple non-transitory computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various one or more of the aspects described above. In some embodiments, computer readable media may be non-transitory media. The non-transitory computer memory or media can be operatively coupled to a hardware processor and can include instructions to perform one or more aspects of the invention.

The terms "program," "software," "application," and "app" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present C Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An ultrasound imaging and therapy guidance system comprising: an ultrasound probe that generates both:
    a two-dimensional ultrasound image frame; and
    a positionally-adjusted ultrasound beam that is automatically adjusted with a mechanical motorized mechanism to acquire three-dimensional image data of bone anatomy in a human subject;
    a therapy applicator to deliver a therapy to the human subject;
    a processor;
    a non-transitory computer memory operatively coupled to the processor, the non-transitory memory comprising computer-readable instructions that cause the processor to:
        detect a position and an orientation of three-dimensional bone surface locations based at least in part on the three-dimensional image data and a current position and a current orientation of the ultrasound probe;
        automatically detect a target therapy site relative to the three-dimensional bone surface locations;
        determine a position and an orientation of the therapy applicator to deliver the therapy to the target therapy site; and
        generate display data;
    a display in electrical communication with the processor, the display generating images based on the display data, the images comprising:
        an indication of the three-dimensional bone surface locations;
            the two-dimensional ultrasound image frame co-aligned with a potential therapy field for the therapy applicator at a current position and a current orientation of the therapy applicator;
        and an indication of the target therapy site relative to the three-dimensional bone surface locations.

2. The system of claim 1, wherein the computer-readable instructions further cause the processor to automatically detect the target therapy site relative to the three dimensional bone surface locations using a neural network.

3. The system of claim 1, wherein the computer-readable instructions further cause the processor to detect the position and the orientation of the three-dimensional bone surface locations by fitting the three-dimensional image data to a three-dimensional bone model.

4. The system of claim 1, wherein the indication of the three-dimensional bone surface locations are displayed as two-dimensional bone surface images with a third dimension encoded to represent a bone surface location along the third dimension.

5. The system of claim 4, wherein the third dimension is graphically encoded to represent the bone surface location along the third dimension.

6. The system of claim 5, wherein the third dimension is color encoded to represent the bone surface location along the third dimension.

7. The system of claim 1, wherein the position and the orientation of the therapy applicator are determined based at least in part on a predetermined relative position of the therapy applicator with respect to the ultrasound probe.

8. The system of claim 1, wherein the images generated by the display further include a current position and a current orientation of the potential therapy field.

9. The system of claim 1, wherein the images generated by the display further include the current position and the current orientation of the therapy applicator.

10. The system of claim 1, wherein the images generated by the display further include dimensional and orientation information of the bone anatomy calculated from the three-dimensional bone surface locations.

11. The system of claim 1, wherein the therapy applicator comprises at least one of a needle guide, a needle, an ablation instrument, or a high-intensity focused ultrasound transducer.

12. The system of claim 1, wherein the target therapy site includes an epidural space, an intrathecal space, or a medial branch nerve.

13. The system of claim 1, wherein the ultrasound probe is configured to be positionally adjusted manually by a user.

14. The system of claim 1, wherein an object tracker includes inductive proximity sensors.

15. The system of claim 1, wherein an object tracker includes an ultrasound image processing circuit.

16. The system of claim 15, wherein the ultrasound image processing circuit is configured to determine a relative change in the current position of the ultrasound probe by comparing sequentially-acquired ultrasound images of the three-dimensional image data.

17. The system of claim 1, wherein the ultrasound imaging and therapy guidance system further comprises an object tracker configured to detect the current position and the current orientation of the ultrasound probe.

18. The system of claim 1, wherein the ultrasound imaging and therapy guidance system further comprises a mechanical apparatus coupled to the ultrasound probe and the therapy applicator to set a predetermined relative position of the therapy applicator with respect to the ultrasound probe.

19. The system of claim 1, wherein the images further comprise graphical indicators that indicate whether the target therapy site and potential therapy field are aligned.

* * * * *